US006448028B1

(12) United States Patent
Squires et al.

(10) Patent No.: US 6,448,028 B1
(45) Date of Patent: Sep. 10, 2002

(54) ENZYMES AND METABOLITES INVOLVED IN SKATOLE METABOLISM

(75) Inventors: E. James Squires, Guelph; Gonzalo J. Diaz, Bogota, both of (CA)

(73) Assignee: University of Guelph, Guelph (CA)

( * ) Notice: Subject to any disclaimer, the term of this patent is extended or adjusted under 35 U.S.C. 154(b) by 0 days.

(21) Appl. No.: 09/672,039

(22) Filed: Sep. 29, 2000

Related U.S. Application Data

(60) Provisional application No. 60/156,935, filed on Sep. 30, 1999.

(51) Int. Cl.[7] ............................. C12Q 1/26; C12Q 1/00; G01N 33/53; C12N 9/00
(52) U.S. Cl. ............................... 435/25; 435/4; 435/7; 435/183; 435/189
(58) Field of Search ............................... 435/7, 18, 25, 435/183, 190

(56) References Cited

U.S. PATENT DOCUMENTS 4,906,563 A    3/1990    Singh

FOREIGN PATENT DOCUMENTS

CA            2234349    10/1999

OTHER PUBLICATIONS

Diaz, Gonzalo J et al., Identification of phase I metabolites of 3–methylindole produced by pig liver microsomes. *Drug Metabolism and Disposition*, v. 27, No. 10, Oct. 1999, pp 1150–1156.

Diaz, Gonzalo J et al., Metabolism of 3–methylindole by porcine liver microsomes: Responsible cytochrome P450 enzymes, *Toxicological Sciences*, vol. 55, No. 2, Jun. 2000, pp 284–292.

Diaz, Gonzalo J et al., Role of aldehyde oxidase in the hepatic in vitro metabolism of 3–methylindole in pigs, *Journal of Agricultural and Food Chemistry*, vol. 48, No. 3, Mar. 2000, pp 833–837.

Database WPI AN 1996 107098 Fremgangsmade til at undersoge grise for at bestemme om de er egnet til avl eller formering samt anvendelse af dyr eller saed (Slagteriernes Forskningsinstitut), May 28, 1996.

Thornton–Manning, Janice et al., Metabolism of 3–methylindole by vaccinia–expressed p450 enzymes: Correlation of 3–methyleneindolenine formation and protein–binding, *Journal of Pharmacology and Experimental Therapeutics*, vol. 276, No. 1, 1996, pp 21–29.

Skordos, Konstantine, W. et al. Evidence supporting the formation of 2,3–epoxy–3–methylindoline: A reactive intermediate of the pneumotoxin 3–methylindole, *Chemical Research in Toxicoloy*, vol. 11, No. 7, Jul. 7, 1998 pp 741–749.

Potchoiba, M.J. et al., Metabolism and Pneumo Toxicity of 3 Methyl Oxindole Indole 3 Carbinol and 3 methyl indole in goats, *American Journal of Veterinary Research*, vol. 43, No. 8, 1982, pp 1418–1423.

*Primary Examiner*—Rebecca E. Prouty
*Assistant Examiner*—Manjunath N. Rao
(74) *Attorney, Agent, or Firm*—Bereskin & Parr

(57) ABSTRACT

Novel metabolites and enzymes involved in skatole metabolism are disclosed. The novel metabolites are 3-OH-3-methylindolenine (HMI); 3-methyloxindole (3MOI); indole-3-carbinol (I-3C); and 2-aminoacetophenone (2-AM). Measuring levels of these metabolites in a pig may be useful in identifying the pig's ability to metabolize skatole and its susceptibility to boar taint. The novel enzymes involved in skatole metabolism are aldehyde oxidase and CYP2A6. Enhancing the activity of these enzymes may be useful in enhancing skatole metabolism and reducing boar taint. The identification of the enzyme also allows the development of screening assays for substances that interact with these enzymes and skatole metabolism. Pigs having high levels of these enzymes may be selected and bred to produce pigs that have a lower incidence of boar taint.

3 Claims, 10 Drawing Sheets

3-Hydroxy-3-methyloxindole (HMOI)

↑ Aldehyde oxidase

3-Hydroxy-3-methylindolenine (HMI)

ENZYMES AND METABOLITES INVOLVED IN SKATOLE METABOLISM

This application claims benefit from U.S. provisional application No. 60/156,935, filed Sep. 30, 1999 which is incorporated herein by reference.

FIELD OF THE INVENTION

The present invention relates to novel metabolites of skatole and the identification of novel enzymes involved in the metabolism of skatole. The invention has utility in developing methods to identify and reduce boar taint.

BACKGROUND OF THE INVENTION

Male pigs that are raised for meat production are usually castrated shortly after birth to prevent the development of off-odors and off flavors (boar taint) in the carcass. Boar taint is primarily due to high levels of either the 16-androstene steroids (especially 5α (-androst-16-en-3-one)) or skatole in the fat. Recent results of the EU research program AIR 3-PL94-2482 suggest that skatole contributes more to boar taint than androstenone (Bonneau, M., 1997).

Skatole is produced by bacteria in the hindgut which degrade tryptophan that is available from undigested feed or from the turnover of cells lining the gut of the pig (Jensen and Jensen, 1995). Skatole is absorbed from the gut and metabolised primarily in the liver (Jensen and Jensen, 1995). High levels of skatole can accumulate in the fat, particularly in male pig, and the presence of a recessive gene $Ska^1$, which results in decreased metabolism and clearance of skatole has been proposed (Lundström et al., 1994; Friis, 1995). Skatole metabolism has been studied extensively in ruminants (Smith, et al., 1993), where it can be produced in large amounts by ruminal bacteria and results in toxic effects on the lungs (reviewed in Yost, 1989). The metabolic pathways involving skatole have not been well described in pigs. In particular, the reasons why only some intact male pigs have high concentrations of skatole in the fat are not clear. Environmental and dietary factors are important (Kjeldsen, 1993; Hansen et al., 1995) but do not sufficiently explain the reasons for the variation in fat skatole concentrations in pigs. Claus et al. (1994) proposed high fat skatole concentrations are a result of an increased intestinal skatole production due to the action of androgens and glucocorticoids. Lundström et al. (1994) reported a genetic influence on the concentrations of skatole in the fat, which may be due to the genetic control of the enzymatic clearance of skatole. The liver is the primary site of metabolism of skatole and liver enzymatic activities could be the controlling factor of skatole deposition in the fat. Bæk et al. (1995) described several liver metabolites of skatole found in blood and urine with the major being MII and MIII. MII, which is a sulfate conjugate of 6-hydroxyskatole (pro-MII), was only found in high concentrations in plasma of pigs which were able to rapidly clear skatole from the body, whereas high MIII concentrations were related to slow clearance of skatole. Thus the capability of synthesis of MII could be a major step in a rapid metabolic clearance of skatole resulting in low concentrations of skatole in fat and consequently low levels of boar taint.

In view of the foregoing, further work is needed to fully understand the metabolism of skatole in pig liver and to identify the key enzymes involved. Understanding the biochemical events involved in skatole metabolism can lead to novel strategies for treating, reducing or preventing boar taint. In addition, polymorphisms in these candidate genes may be useful as possible markers for low boar taint pigs.

SUMMARY OF THE INVENTION

The present inventors have identified novel metabolites resulting from the phase I metabolism of skatole (3-methylindole, 3MI) by porcine liver microsomes. The metabolites identified are: 3-OH-3-methylindolenine (HMI); 3-methyloxindole (3MOI); indole-3-carbinol (I-3C); and 2-aminoacetophenone (2-AM). Measuring levels of these metabolites in a pig may be useful in identifying the pig's ability to metabolize skatole and hence its susceptibility to boar taint.

The present inventors have also determined that one of the metabolites of skatole, HMI is metabolized to 3-hydroxy-3-methyloxindole (HMOI) by aldehyde oxidase. As a result, enhancing the activity of the aldehyde oxidase may be useful in enhancing skatole metabolism and reducing boar taint. Accordingly, the present invention provides a method for enhancing the metabolism of 3-methylindole and thereby reducing boar taint comprising enhancing the activity of aldehyde oxidase in a pig. The activity of aldehyde oxidase can be enhanced by using substances which (a) increase the activity of aldehyde oxidase; or (b) induce or increase the expression of the aldehyde oxidase gene.

The present inventors have further determined that the cytochrome P450 enzyme, CYP2A6, is also involved in the metabolism of skatole by porcine liver microsomes. As a result, enhancing the activity of the CYP2A6 may be useful in enhancing skatole metabolism and reducing boar taint. Accordingly, the present invention provides a method for enhancing the metabolism of 3-methylindole and thereby reducing boar taint comprising enhancing the activity of CYP2A6 in a pig. The activity of CYP2A6 can be enhanced by using substances which (a) increase the activity of CYP2A6; or (b) induce or increase the expression of the CYP2A6 gene.

The identification of enzymes involved in the metabolism of skatole allows the development of screening assays for substances that interact with these enzymes in skatole metabolism. The screening assays can be used to identify substances that can be used to reduce or treat boar taint.

The present invention also includes a method for producing pigs that have a lower incidence of boar taint by selecting pigs that have high levels of aldehyde oxidase and/or CYP2A6 and breeding the selected pigs.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

I. Skatole Metabolites

Figure 1:
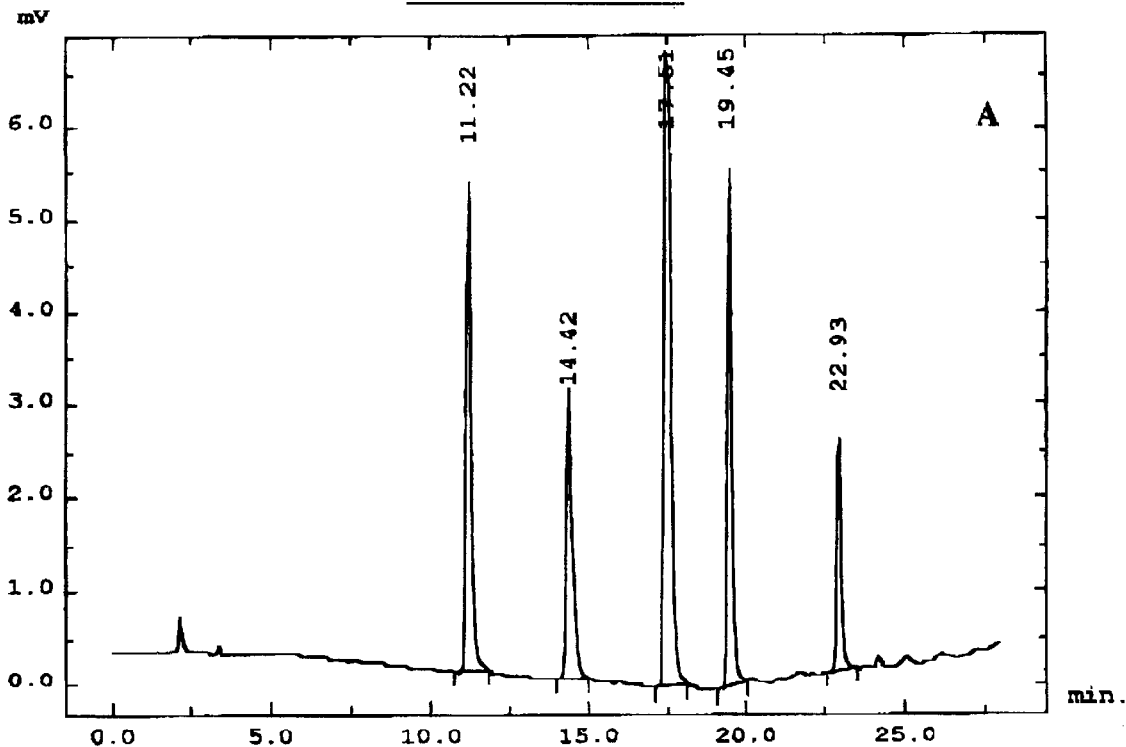
FIG. 1 is a chromatographic profile of the main five metabolites produced by pig liver microsomes as detected by UV absorption at 250 nm. Retention times correspond as follows: 9.16 min, UV-1; 11.24 min, 3-hydroxy-3-methyloxindole; 14.42 min, indole-3-carbinol; 17.51 min, 3-methyloxindole; 19.43 min, 2-aminoacetophenone; 22.84 min, parent compound (3-methylindole). (A) Standard mixture containing 2 μg/ml of each metabolite. (B) Incubation mixture.
Figure 1:
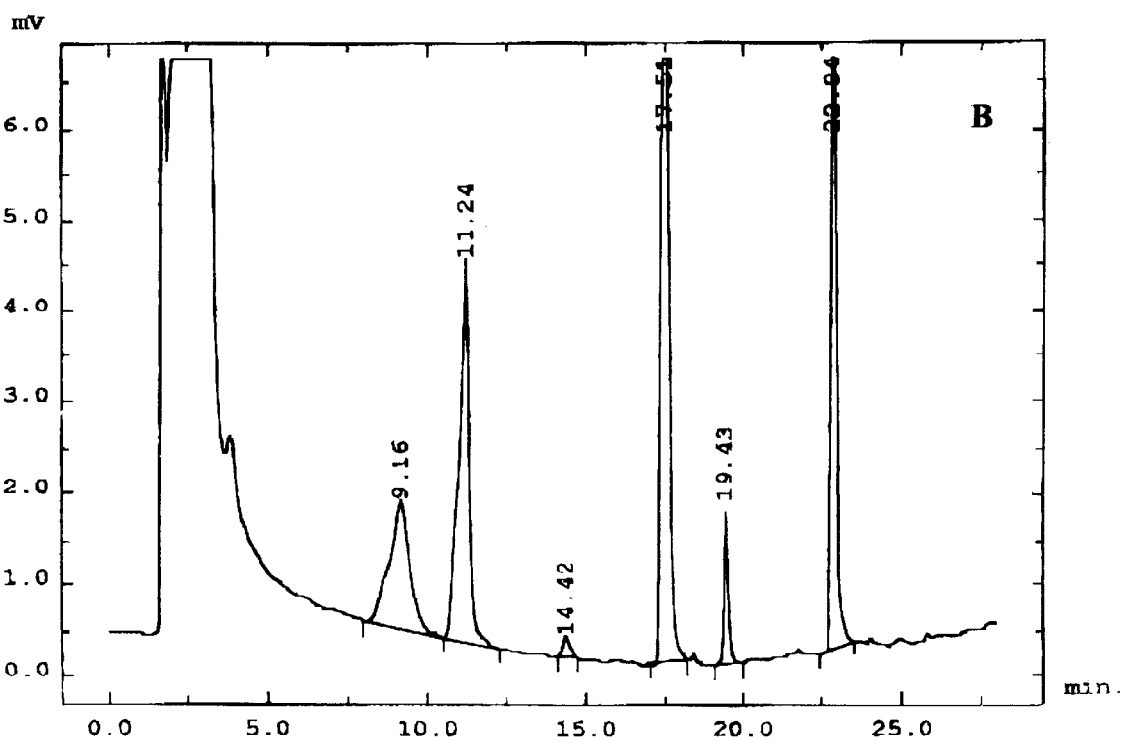

The present inventors have identified novel metabolites resulting from the phase I metabolism of skatole (3-methyl indole, 3MI) by porcine liver microsomes. The metabolites identified are: 3-OH-3-methylindolenine (HMI); 3-methyloxindole (3MOI); indole-3-carbinol (I-3C); and 2-aminoacetophenone (2-AM).

Measuring levels of these metabolites in a pig may be useful in identifying the pig's ability to metabolize skatole and its susceptibility to boar taint. Accordingly, the present invention provides a method of assessing a pig's ability to metabolize 3-methyl indole comprising testing a sample from the pig for one or more metabolites selected from the group consisting of 3-OH-3-methylindolenine (HMI); 3-methyloxindole (3MOI); indole-3-carbinol (I-3C); and 2-aminoacetophenone.

Since skatole metabolites also undergo Phase II sulfation and glucuronidation reactions, the assay may include measuring the sulfation or glucuronidation products of the metabolites. The sample can be any biological sample from the pig, preferably liver, plasma or fat. Measuring levels of particular metabolites can be used to classify pigs as either good or poor skatole metabolizers. Poor skatole metabolism may be causative of boar taint and therefore the assay may be useful in identifying pigs with boar taint or at risk for developing poor taint. Pigs that have a reduced risk for boar taint (i.e., good metabolizers) may be further selected and bred to produce low boar taint pigs.

II. Enzymes a) Aldehyde Oxidase

The present inventors have determined that one of the metabolites of skatole, HMI is metabolized to 3-hydroxy-3-methyloxindole (HMOI) by aldehyde oxidase, a cytosolic metalloflavoprotein. The inventors have also determined that aldehyde oxidase plays an important role in the metabolism of skatole (or 3MI) and that its catalytic activity is related to adequate 3MI clearance. As a result, enhancing the activity of the aldehyde oxidase may be useful in enhancing skatole metabolism and reducing boar taint. Accordingly, the present invention provides a method for enhancing the metabolism of 3-methylindole comprising enhancing the activity of aldehyde oxidase in a pig. The activity of aldehyde oxidase can be enhanced by using substances which (a) increase the activity of aldehyde oxidase; or (b) induce or increase the expression of the aldehyde oxidase gene. The activity of aldehyde oxidase may also be enhanced using gene therapy whereby a nucleic acid sequence encoding an dehyde oxidase enzyme in introduced into a pig either ex-vivo or in-vivo. A nucleic acid sequence encoding aldehyde oxidase may be obtained by cloning the pig gene using the information available from the human, bovine and rabbit genes.

As mentioned above, aldehyde oxidase activity is related to 3MI clearance. As a result, testing the enzymatic activity of aldehyde oxidase in a pig can be used to determine a pig's susceptibility to boar taint. Pigs with high aldehyde oxidase activity would be at a lower risk for boar taint than pigs with a low aldehyde oxidase activity. Pigs with high aldehyde oxidase activity may be selected and bred to produce low boar taint pigs. Accordingly, the present invention provides a method of determining a pig's susceptibility to boar taint comprising determining the activity of aldehyde oxidase in a sample from a pig. Methods for determining aldehyde oxidase activity are detailed in Example 2.

b) CYP2A6

The present inventors have further determined that the cytochrome P450 enzyme, CYP2A6, is also involved in the metabolism of skatole by porcine liver microsomes. As a result, enhancing the activity of CYP2A6 may be useful in enhancing skatole metabolism and reducing boar taint. Accordingly, the present invention provides a method for enhancing the metabolism of 3-methylindole comprising enhancing the activity of CYP2A6 in a pig. The activity of CYP2A6 can be enhanced by using substances which (a) increase the activity of CYP2A6; or (b) induce or increase the expression of the CYP2A6 gene. The activity of CYP2A6 may also be enhanced using gene therapy whereby a nucleic acid sequence encoding a CYP2A6 enzyme in introduced into a pig either ex-vivo or in-vivo. A nucleic acid sequence encoding CYP2A6 may be obtained by cloning the pig gene using the information available from the human gene.

Testing the enzymatic activity of CYP2A6 in a pig can be used to determine a pig's susceptibility to boar taint. Pigs with high CYP2A6 activity would be at a lower risk for boar taint than pigs with a low CYP2A6 activity. Pigs with high CYP2A6 activity may be selected and bred to produce low boar taint pigs. Accordingly, the present invention provides a method of determining a pig's susceptibility to boar taint comprising determining the activity of CYP2A6 in a sample from a pig.

c) Screening Assays

The identification of enzymes involved in the metabolism of skatole allows the development of screening assays for substances that interact with these enzymes and thereby modulate skatole metabolism.

In one aspect, the present invention provides a method of screening for a substance that enhances the activity of aldehyde oxidase or CYP2A6.

In one embodiment of the invention, a method is provided for screening for a substance that enhances skatole metabolism in a pig by enhancing aldehyde oxidase activity comprising the steps of:

(a) reacting a substrate of aldehyde oxidase and aldehyde oxidase, in the presence of a test substance, under conditions such that aldehyde oxidase is capable of converting the substrate into a reaction product;

(b) assaying for reaction product, unreacted substrate or unreacted aldehyde oxidase;

(c) comparing to controls to determine if the test substance selectively enhances aldehyde oxidase activity and thereby is capable of enhancing skatole metabolism in a pig.

Substrates of aldehyde oxidase which may be used in the method of the invention include HMI which is metabolized to HMOI.

The induction of aldehyde oxidase activity can be measured using a variety of techniques including measuring the levels of the aldehyde oxidase protein or mRNA or by testing for aldehyde oxidase activity. Aldehyde oxidase activity can be measured using various assays including the assay described in Example 2 and those described by Rajagopalan et al., 1966.

In another embodiment of the invention, a method is provided for screening for a substance that enhances skatole metabolism in a pig by enhancing CYP2A6 activity comprising the steps of:

(a) reacting a substrate of CYP2A6 and CYP2A6, in the presence of a test substance, under conditions such that CYP2A6 is capable of converting the substrate into a reaction product;

(b) assaying for reaction product, unreacted substrate or unreacted CYP2A6;

(c) comparing to controls to determine if the test substance selectively enhances CYP2A6 activity and thereby is capable of enhancing skatole metabolism in a pig.

Substrates of CYP2A6 which may be used in the method of the invention for example include skatole and coumarin.

The induction of CYP2A6 activity can be measured using a variety of techniques including measuring the levels of the CYP2A6 protein or mRNA or by testing for CYP2A6 activity as described in Aitio, 1978.

The aldehyde oxidase and CYP2A6 enzymes used in the method of the invention may be obtained from natural, recombinant, or commercial sources. Cells or liver microsomes expressing the enzymes may also be used in the method.

Conditions which permit the formation of a reaction product may be selected having regard to factors such as the nature and amounts of the test substance and the substrate.

The reaction product, unreacted substrate, or unreacted enzyme; may be isolated by conventional isolation techniques, for example, salting out, chromatography, electrophoresis, gel filtration, fractionation, absorption, polyacrylamide gel electrophoresis, agglutination, or combinations thereof.

To facilitate the assay of the reaction product, unreacted substrate, or unreacted enzyme; antibody against the reaction product or the substance, or a labelled enzyme or substrate, or a labelled substance may be utilized. Antibodies, enzyme, substrate, or the substance may be labelled with a detectable marker such as a radioactive label, antigens that are recognized by a specific labelled antibody, fluorescent compounds, enzymes, antibodies specific for a labelled antigen, and chemiluminescent compounds.

The substrate used in the method of the invention may be insolubilized. For example, it may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insolubilized enzyme, substrate, or substance may be prepared by reacting the material with a suitable insoluble carrier using known chemical or physical methods, for example, cyanogen bromide coupling.

In another aspect, the present invention includes a method for screening for a substance that enhances skatole metabolism by modulating the transcription or translation of an enzyme involved in skatole metabolism.

In one embodiment of the invention, a method is provided for screening for a substance that enhances skatole metabolism by enhancing transcription and/or translation of the gene encoding aldehyde oxidase comprising the steps of:

(a) culturing a host cell comprising a nucleic acid molecule containing a nucleic acid sequence encoding aldehyde oxidase and the necessary elements for the transcription or translation of the nucleic acid sequence, and optionally a reporter gene, in the presence of a test substance; and (b) comparing the level of expression of aldehyde oxidase, or the expression of the protein encoded by the reporter gene with a control cell transfected with a nucleic acid molecule in the absence of the test substance.

In another embodiment of the invention, a method is provided for screening for a substance that enhances skatole metabolism by enhancing transcription and/or translation of the gene encoding CYP2A6 comprising the steps of:

(a) culturing a host cell comprising a nucleic acid molecule containing a nucleic acid sequence encoding CYP2A6 and the necessary elements for the transcription or translation of the nucleic acid sequence, and optionally a reporter gene, in the presence of a test substance; and (b) comparing the level of expression of CYP2A6, or the expression of the protein encoded by the reporter gene with a control cell transfected with a nucleic acid molecule in the absence of the test substance.

A host cell for use in the method of the invention may be prepared by transfecting a suitable host with a nucleic acid molecule comprising a nucleic acid sequence encoding the appropriate enzyme. Suitable transcription and translation elements may be derived from a variety of sources, including bacterial, fungal, viral, mammalian, or insect genes. Selection of appropriate transcription and translation elements is dependent on the host cell chosen, and may be readily accomplished by one of ordinary skill in the art. Examples of such elements include: a transcriptional promoter and enhancer or RNA polymerase binding sequence, a ribosomal binding sequence, including a translation initiation signal. Additionally, depending on the host cell chosen and the vector employed, other genetic elements, such as an origin of replication, additional DNA restriction sites, enhancers, and sequences conferring inducibility of transcription may be incorporated into the expression vector. It will also be appreciated that the necessary transcription and translation elements may be supplied by the native gene of the enzyme and/or its flanking sequences.

Examples of reporter genes are genes encoding a protein such as green fluorescence protein, β-galactosidase, chloramphenicol acetyltransferase, firefly luciferase, or an immunoglobulin or portion thereof such as the Fc portion of an immunoglobulin, preferably IgG. Transcription of the reporter gene is monitored by changes in the concentration of the reporter protein such as β-galactosidase, chloramphenicol acetyltransferase, or firefly luciferase. This makes it possible to visualize and assay for expression of the enzyme and in particular to determine the effect of a substance on expression of enzyme.

Suitable host cells include a wide variety of prokaryotic and eukaryotic host cells, including bacterial, mammalian, yeast or other fungi, viral, plant, or insect cells. Protocols for the transfection of host cells are well known in the art (see, Sambrook et al. Molecular Cloning A Laboratory Manual, 2nd edition, Cold Spring Harbor Laboratory Press, 1989, which is incorporated herein by reference). Host cells which are commercially available may also be used in the method of the invention. For example, the h2A3 and h2B6 cell lines available from Gentest Corporation are suitable for the screening methods of the invention.

Substances which enhance skatole metabolism by enhancing aldehyde oxidase or CYP2A6 activity (including the substances isolated by the above screening methods) may be used to reduce or treat boar taint or to prepare medicaments to reduce or treat boar taint.

d) Compositions

Substances which enhance skatole metabolism (including substances identified using the methods of the invention which selectively enhance aldehyde oxidase or CYP2A6 activity) may be incorporated into pharmaceutical compositions. Therefore, the invention provides a pharmaceutical composition for use in reducing boar taint comprising an effective amount of one or more substances which enhance skatole metabolism and a pharmaceutically acceptable carrier, diluent, or excipient. The term "effective amount" as used herein means an amount effective, at dosages and for periods of time necessary to achieve the desired result.

In one embodiment, the present invention provides a pharmaceutical composition comprising an effective amount of a substance which is selected from the group consisting of (a) a substance that increases the activity of an aldehyde oxidase enzyme;

(b) a substance that induces or increases the expression of an aldehyde oxidase gene;

(c) a substance that increases the activity of an CYP2A6 enzyme; and (d) a substance that induces or increases the expression of an CYP2A6 gene.

The substances for the present invention can be administered for oral, topical, rectal, parenteral, local, inhalant or intracerebral use. Preferably, the active substances are administered orally (in the food or drink) or as an injectable formulation.

In the methods of the present invention, the substances described in detail herein and identified using the method of the invention form the active ingredient, and are typically administered in admixture with suitable pharmaceutical diluents, excipients, or carriers suitably selected with respect to the intended form of administration, that is, oral tablets, capsules, elixirs, syrups and the like, consistent with conventional veterinary practices.

For example, for oral administration the active ingredients may be prepared in the form of a tablet or capsule for inclusion in the food or drink. In such a case, the active substances can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral active substances can be combined with any oral, non-toxic, pharmaceutically acceptable inert carrier such as ethanol, glycerol, water, and the like. Suitable binders, lubricants, disintegrating agents, and coloring agents can also be incorporated into the dosage form if desired or necessary. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Suitable lubricants used in these dosage forms include sodium oleate, sodium stearate, magnesium stearate, sodium benzoate, sodium acetate, sodium chloride, and the like. Examples of disintegrators include starch, methyl cellulose, agar, bentonite, xanthan gum, and the like.

Gelatin capsules may contain the active substance and powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain coloring and flavoring agents to increase acceptance.

Water, a suitable oil, saline, aqueous dextrose, and related sugar solutions and glycols such as propylene glycol or polyethylene glycols, may be used as carriers for parenteral solutions. Such solutions also preferably contain a water soluble salt of the active ingredient, suitable stabilizing agents, and if necessary, buffer substances. Suitable stabilizing agents include antioxidizing agents such as sodium bisulfate, sodium sulfite, or ascorbic acid, either alone or combined, citric acid and its salts and sodium EDTA. Parenteral solutions may also contain preservatives, such as benzalkonium chloride, methyl- or propyl-paraben, and chlorobutanol.

The substances described in detail herein and identified using the methods of the invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Substances described in detail herein and identified using the methods of the invention may also be coupled with soluble polymers which are targetable drug carriers. Examples of such polymers include polyvinylpyrrolidone, pyran copolymer, polyhydroxypropyl-methacrylamidephenol, polyhydroxyethyl-aspartamidephenol, or polyethyleneoxide-polylysine substituted with palmitoyl residues. The substances may also be coupled to biodegradable polymers useful in achieving controlled release of a drug. Suitable polymers include polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Suitable pharmaceutical carriers and methods of preparing pharmaceutical dosage forms are described in *Remington's Pharmaceutical Sciences*, Mack Publishing Company, a standard reference text in this field.

More than one substance described in detail herein or identified using the methods of the invention may be used to enhance metabolism of skatole. In such cases the substances can be administered by any conventional means available for the use in conjunction with pharmaceuticals, either as individual separate dosage units administered simultaneously or concurrently, or in a physical combination of each component therapeutic agent in a single or combined dosage unit. The active agents can be administered alone, but are generally administered with a pharmaceutical carrier selected on the basis of the chosen route of administration and standard pharmaceutical practice as described herein.

e) Genetic Screening

The present invention further includes the identification of polymorphisms in genes encoding the enzymes responsible for skatole metabolism in a pig including aldehyde oxidase and CYP2A6 as described in detail hereinabove. The identification of genes that encode these enzymes from pigs that are high skatole metabolizers (and hence have a low incidence of low boar taint) can be used to develop lines of pigs that have a low incidence of boar taint. In addition, the identification of these genes can be used as markers for identifying pigs that are predisposed to having a low incidence of boar taint.

Accordingly, the present invention provides a method for producing pigs which have a lower incidence of boar taint comprising selecting pigs that express high levels of aldehyde oxidase and/or CYP2A6; and breeding the selected pigs.

Transgenic pigs may also be prepared which produce high levels of aldehyde oxidase and/or CYP2A6. The transgenic pigs may be prepared using conventional techniques. For example, a recombinant molecule may be used to introduce (a) a gene encoding aldehyde oxidase or (b) a gene encoding a CYP2A6. Such recombinant constructs may be introduced into cells such as embryonic stem cells, by a technique such as transfection, electroporation, injection, etc. Cells which show high levels of aldehyde oxidase and/or CYP2A6 may be identified for example by Southern Blotting, Northern Blotting, or by other methods known in the art. Such cells may then be fused to embryonic stem cells to generate transgenic animals. Germline transmission of the mutation may be achieved by, for example, aggregating the embryonic stem cells with early stage embryos, such as eight cell embryos, transferring the resulting blastocysts into recipient females in vitro, and generating germline transmission of the resulting aggregation chimeras. Such a transgenic pig may be mated with pigs having a similar phenotype i.e. producing high levels of aldehyde oxidase and/or CYP2A6 to produce animals having a low incidence of boar taint.

The following non-limiting examples are illustrative of the present invention:

EXAMPLES

Example 1

Identification of Skatole Metabolites

Materials And Methods

Chemicals. 3-Methylindole (3MI), indole-3-carbinol (I3C), indole-3-aldehyde, indole-3-carboxylic acid, 2-aminoacetophenone and sulfatase type H-2 from *Helix pomatia* were purchased from Sigma-Aldrich Canada Ltd. (Oakville, ON, Canada). The oxindoles, 3-methyloxindole (3MOI) and 3-hydroxy-3-methyloxindole (HMOI) were synthesized by the methods of Kende and Hodges (1982) and Skiles et al. (1989), respectively. Authentic 5-OH-3-methylindole and 6-OH-3-methylindole (in the form of 6-sulfatoxyskatole) were donated by Jens Hansen-Møller (Danish Meat Research Institute, Roskilde, Denmark). In order to obtain 6-OH-3-methylindole from 6-sulfatoxyskatole, the compound was hydrolyzed in a total volume of 0.5 ml acetate buffer pH 5.0 containing 90 units/ml of type H-2 sulfatase. Hydrolysis was conducted for 4 hours in a shaking water bath at 40° C. and then 0.5 ml of ice-cold acetonitrile were added both to stop the reaction and precipitate the protein. After centrifugation at 7,500 rpm for 15 min, 50 µl of clear supernatant were injected into the chromatograph, using the conditions described below under "Analytical chromatography".

Preparation of microsomes. Liver samples were taken from 30 intact male pigs obtained by back-crossing F3 European Wild Pig×Swedish Yorkshire boars with Swedish Yorkshire sows (Squires and Lundström, 1997). Liver samples were frozen in liquid nitrogen and stored at −80° C. For the preparation of microsomes, partially thawed liver samples were finely minced and homogenized with 4 volumes of 0.05 M Tris-HCl buffer pH 7.4 (containing 0.15 M KCl, 1 mM EDTA, and 0.25 M sucrose) using a Ultra-Turax homogenizer (Janke and Kunkel, GDR). The homogenate was centrifuged at 10,000 g for 20 min and the resulting supernatant was centrifuged again at 100,000 g for 60 min order to obtain the microsomal pellet. The pellets were suspended in a 0.05 M Tris-HCl buffer, pH 7.4, containing 20% glycerol, 1 mM EDTA, and 0.25 M sucrose to a final concentration of 20 mg protein/ml and stored at −80° C. before analysis. Protein concentrations were determined by the method of Smith et al. (1985) using bicinchoninic acid protein assay reagents purchased from Pierce Chemical Co. (Rockford, Ill., USA) and bovine serum albumin as standard.

Microsomal incubations. Two mg microsomal protein was incubated with 0.4 mM 3MI and 4 mM NADPH in 0.05M sodium phosphate buffer (pH 7.4) containing 5 mM $MgCl_2$ and 1 mM EDTA for 30 min at 37° C. (production of metabolites was determined to be linear over a range of 10 to 40 min). Incubation volumes were 0.5 ml. Reactions were started by the addition of NADPH after 3-minute preincubation periods at 37° C., and stopped with 0.5 ml of ice-cold acetonitrile. Incubations of all 30 samples were run in duplicate and for control incubations NADPH was omitted. After the addition of acetonitrile the mixture was vortexed and centrifuged at 5000 rpm for 20 min. A 50 µl aliquot of the clear supernatant was analyzed by high-performance liquid chromatography (HPLC).

Analytical chromatography. Analytical HPLC was done using a Spectra-Physics system (Spectra-Physics, San Jose, Calif., USA) consisting of a SP8800 gradient pump, a SP8880 autosampler with a 50 µl injection loop, a SP Spectra 100 UV detector, and a Spectra System FL-2000 fluorescent detector. The HPLC method is a modification of a previously reported binary gradient system method (Baek et al., 1995). 3MI and its metabolites were separated using a reverse-phase Prodigy ODS, 5 µm, 250×4.6 mm column (Phenomenex, Torrance, Calif., USA). The mobile phase consisted of two solvents, A (0.01M potassium dihydrogen phosphate buffer pH 3.9) and B (acetonitrile), with the following gradients: 0 min —90% A, 6 min—80% A; 12 min—70% A; 18 min—30% A; 25 min 10% A; 26 min 90% A; 35 min—90% A. All gradients were linear and the flow rate was set at 1.2 ml/min. Absorbance was monitored at 250 nm; fluorescence was monitored at excitation and emission wavelengths of 286 and 350 nm, respectively. HPLC analysis for 3MI metabolites was conducted immediately after the incubations. Metabolites were identified by comparison of retention times, and co-injection of standards (spiking the metabolite mixture with authentic standards).

Isolation and purification of metabolites by preparative HPLC. In order to obtain a sufficient amount of metabolites to conduct UV spectral analysis, a large scale incubation (final volume of 4 ml) was performed, using the same concentrations of reactants as described above. Preparative HPLC was done using a Spectra-Physics SP8800 gradient pump (Spectra-Physics, San Jose, Calif., USA), a manual Rheodyne 7125 injector fitted with a 500 µl injection loop (Rheodyne, Cotati, Calif., USA), and a SP Spectra 100 UV detector. The 3MI metabolites were separated using a reverse-phase Waters preparative HPLC C18, 10 µm, 300× 7.6 mm column (Waters Associates, Division of Millipore Corp., Milford, Mass., USA). The mobile phase was the same as above except that the flow rate was set at 3.0 ml/min. The peaks corresponding to the metabolites identified on the basis of their retention times as HMOI, I3C, 3MOI and 2-aminoacetophenone were collected in enough amounts to determine their UV spectra. Purity of the collected fractions was verified by HPLC using the procedure described before under "Analytical chromatography". One of the metabolites produced by pig liver microsomes could not be identified on the basis of comparison of retention times; this metabolite was named UV-1 due to its absorption in the far UV spectrum and the fact that it was the first metabolite that eluted from the column (Babol et al., 1998a). The peak corresponding to this metabolite, which eluted between 9.1 and 10.1 min, was collected after several 500 µl injections and subjected to HPLC-MS, $^1$H-NMR and UV spectra analysis.

Ultraviolet Spectroscopy. UV spectra (200–300 nm) were recorded for the HPLC metabolites UV-1, HMOI, I3C, 3MOI and 2-aminoacetophenone. UV spectra of available authentic standards were also recorded and compared with those of the isolated metabolites. Spectra were recorded on a model 4054 LKB Biochrom UV-Visible spectrophotometer (Pharmacia LKB Biochrom Ltd. Cambridge, UK). Due to their low levels of production, it was not possible to isolate the hydroxyskatoles in enough quantities to determine their UV spectra.

LC/MS of metabolite UV-1. Metabolite UV-1 was analyzed by LC-MS using the following conditions: the HPLC was performed using a Prodigy 5 ODS-2, 5 µm, 150×3.2 mm column (Phenomenex, Torrance, Calif., USA) and water:acetonitrile (50:50) as mobile phase. The mobile phase was delivered by binary LC pumps (Hewlett Packard 1090 Series II/L, Palo Alto, Calif., USA). The eluent passed through a sample injection valve Rheodyne 7010 (Rheodyne, Cotati, Calif., USA), to an atmospheric pressure chemical ionization (APCI) source configured with a corona discharge pin, at a flow rate of 0.7 ml/min. A sample volume of 20 µl was injected by an autosampler (Hewlett Packard 1090 Series II/L, Palo Alto, Calif., USA). Mass spectrometry (MS) detection was achieved using a VG Quattro II triple quadrupole mass spectrometer (Fisons UK Ltd., Altrincham, UK). Instrument control, data acquisition and data processing were carried out using the MassLynx software package. Liquid nitrogen was used as a drying and sheath gas, at flow rates of 200 and 50 liter/hr, respectively. The instrument was operated in the positive ion mode with an ion source temperature of 150° C., a corona discharge pin potential of +3.75 kV, and a cone voltage of 15V. The total ion chromatogram of LC/MS was obtained by scanning the first quadrupole from m/z 125–700 at a rate of 400 amu/sec in full scan mode with inter-scan delay of 0.10 sec. Data was acquired in continuum mode. The production scan was performed by tandem mass spectrometry (MS/MS) by transmitting the protonated molecular ion ([M+H]$^+$) through the first quadrupole into the second quadrupole containing ultrapure argon. The production chromatogram was recorded by scanning the third quadrupole from m/z 50 to 450 in 1.0 sec. The collision energy was varied between −20 to −50 eV to optimize fragmentation of the selected protonated molecular ion.

NMR spectroscopy of metabolite UV-1. UV-1 metabolite was isolated for NMR analysis using incubation conditions essentially as described above. However, these incubations contained 1 nmol cytochrome P450 content rather than 2 mg of total protein. UV-1 was separated from other microsomal 3MI metabolites by the HPLC conditions described above using a system consisting of an LDC Analytical Constametric 4100 solvent delivery module (ThermoQuest, Riviera Beach, Fla., USA), a Hewlett Packard 1040A diode array detector and a Hewlett Packard 9000 series HPLC workstation (Hewlett Packard Company, Willington, Del., USA). UV-1 was purified by HPLC and pooled from two identical incubations followed by concentration in a Savant Speed-Vac (Savant Instruments, Farmingdale, N.Y., USA). Concentration to dryness was not possible, due to polymerization and degradation of unstable UV-1. Therefore, the sample was evaporated to a volume of 200 L and re-injected on the HPLC for additional purification. In this case however, the aqueous mobile phase consisted of 0.01 M dibasic potassium phosphate buffer, pH 9.0, in 99.9 atom % deuterium oxide. Due to the instability of UV-1 when it was evaporated to dryness, it was necessary to perform the final purification step in the NMR solvent, deuterium oxide. UV-1 was again collected and evaporated to a final volume of 250 L and directly added to the Shigemi NMR tube. The $^1$H-NMR spectrum was obtained in deuterium oxide using a Varian Unity Inova 600 MHz NMR (Varian Associates Inc., Palo Alto, Calif., USA).

Results

HPLC. None of the metabolites produced by pig liver microsomes co-eluted with indole-3-carboxaldehyde or indole-3-carboxylic acid. However, metabolites that coeluted with HMOI, 3MOI, I3C, 2-aminoacetophenone, and the two hydroxyskatoles (5- and 6-OH-3-methylindole) were measured by UV and/or fluorescence detection. The oxindole metabolites (HMOI and 3MOI) and the pyrrole ring opened metabolite (2-aminoacetophenone) were detected and quantitated by UV absorption because they do not fluoresce; I3C and the hydroxyskatoles were detected and quantitated by fluorescence detection. When microsomal incubations were spiked, all metabolites identified on the basis of their retention times, co-chromatographed with their corresponding authentic standards. The chromatographic profile of a microsomal incubation and a standard mixture monitored by UV absorption at 250 nm is shown in FIG. 1.

Figure 2:
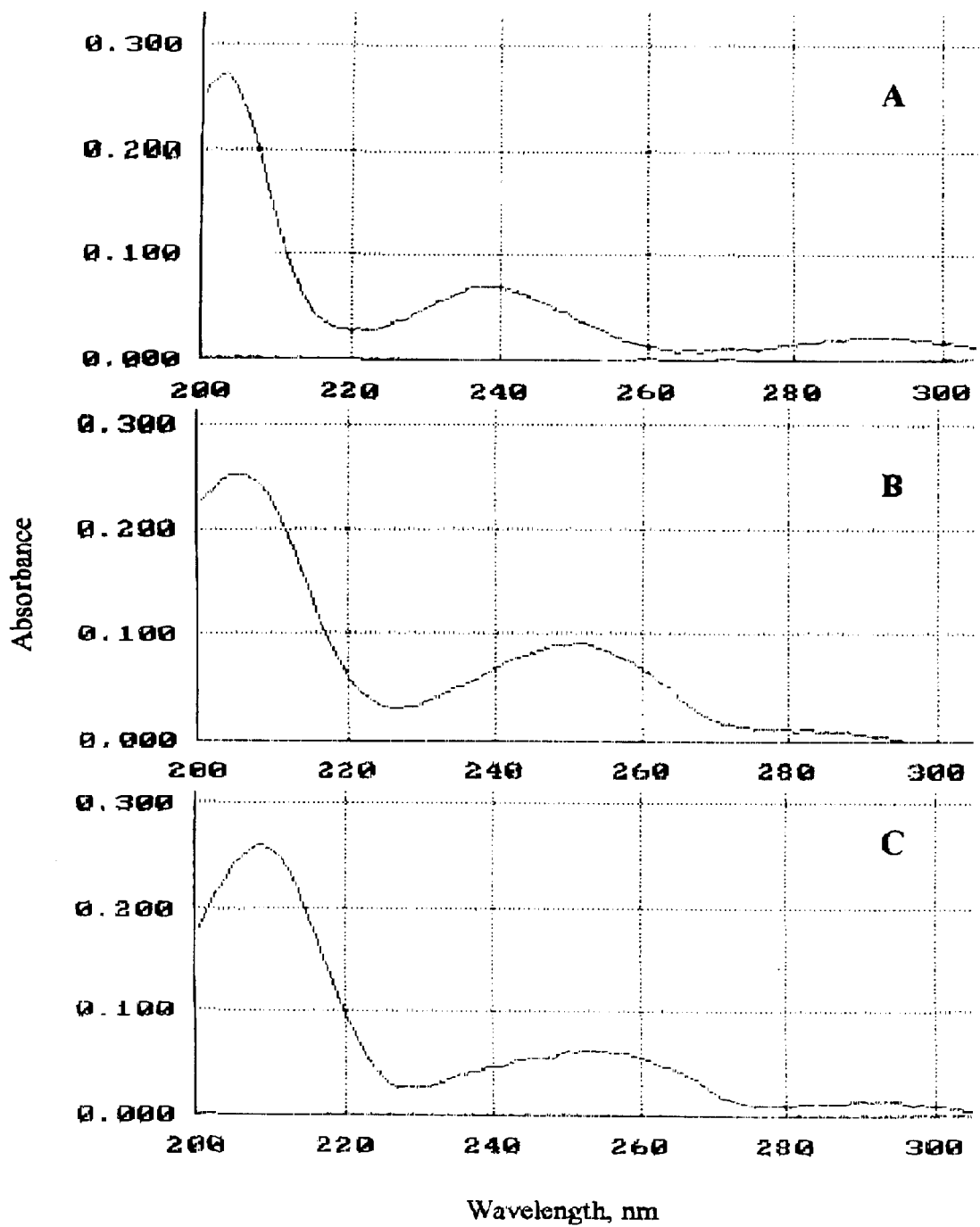
FIG. 2 is a UV spectra of (A) UV-1 metabolite[$\lambda_{max}$ (nm): 204, 238]; (B) 3-methyloxindole[$\lambda_{max}$ (nm): 205, 252]; and (C) 3-hydroxy-3-methyloxindole[HMOI: $\lambda_{max}$ (nm): 208, 253].

UV Spectroscopy. The UV spectrum of the metabolites identified on the basis of their retention times on HPLC (HMOI, 3MOI, I3C, and 2-aminoacetophenone) were identical to those of authentic standards. Spectra of metabolites were recorded using water as solvent, and the wavelengths of maximal absorption were as follows: HMOI: $\lambda_{max}$ (nm): 208, 253; 3MOI: $\lambda_{max}$ (nm): 205, 252; I3C: $\lambda_{max}$ (nm): 221, 278; 2-aminoacetophenone: $\lambda_{max}$ (nm): 228, 257. The UV spectrum of 3-methylindole was: $\lambda_{max}$ (nm): 224, 281. The UV spectrum of UV-1 metabolite was: $\lambda_{max}$ (nm): 204, 238. The UV spectra of UV-1 was similar to the spectra of the oxindole metabolites 3MOI and HMOI as shown in FIG. 2. Changing the pH from 3 to 11 did not change the spectrum of UV-1; this lack of a bathochromic shift indicated that the unknown metabolite had no free phenolic group. Isolated UV-1 was kept in acetonitrile:water solution at room temperature and the solution was analyzed by HPLC at 7-day intervals for 6 weeks. After 6 weeks only about 25% of the original compound remained and it was observed that UV-1 was converted into 3MOI. The slopes of the linear regressions of 3MOI and UV-1 over time indicated that the molar response factor for UV-1 on HPLC-UV analysis was 2.95 times that of 3MOI.

Figure 3:
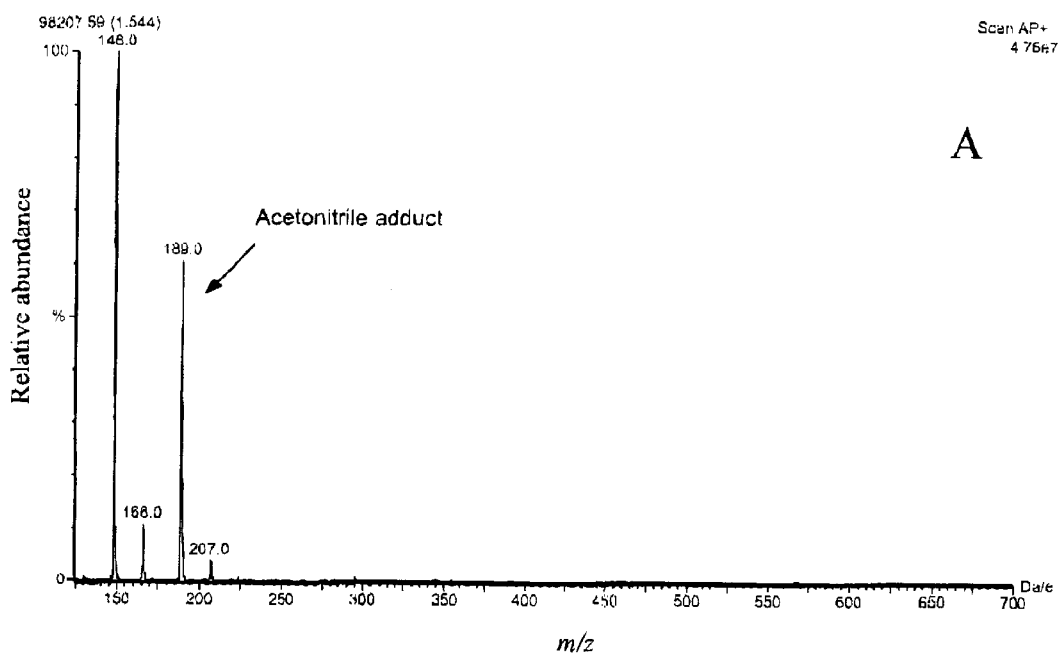
FIG. 3A is an LC-MS spectrum of metabolite UV-1.
FIG. 3B is an MS/MS spectrum of daughter ion of m/z 148.
Figure 3:
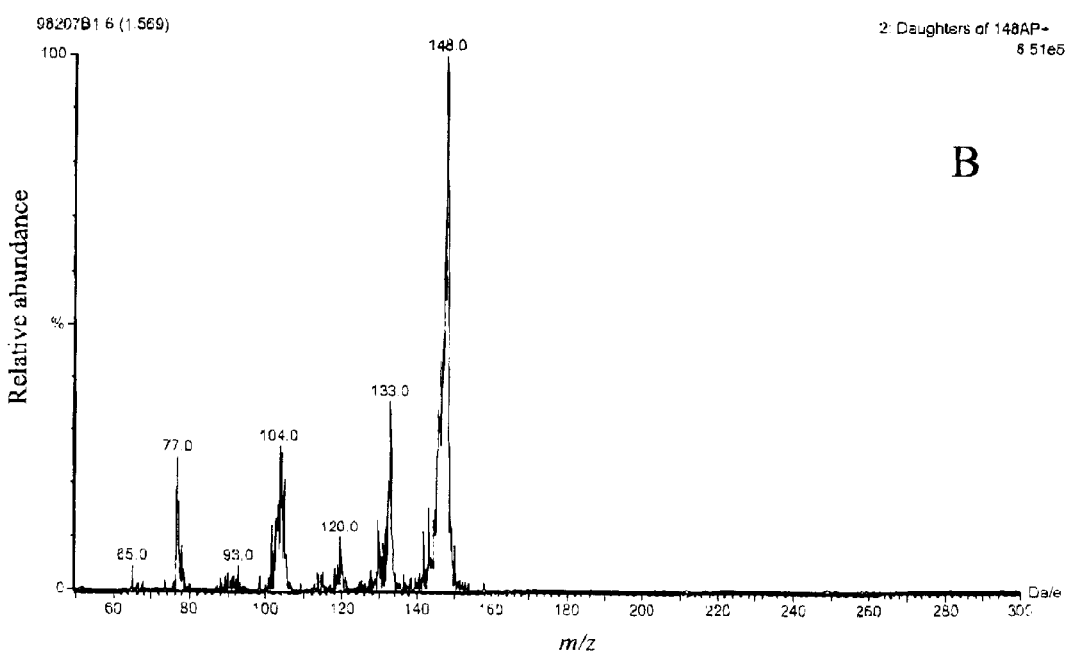
Figure 4:
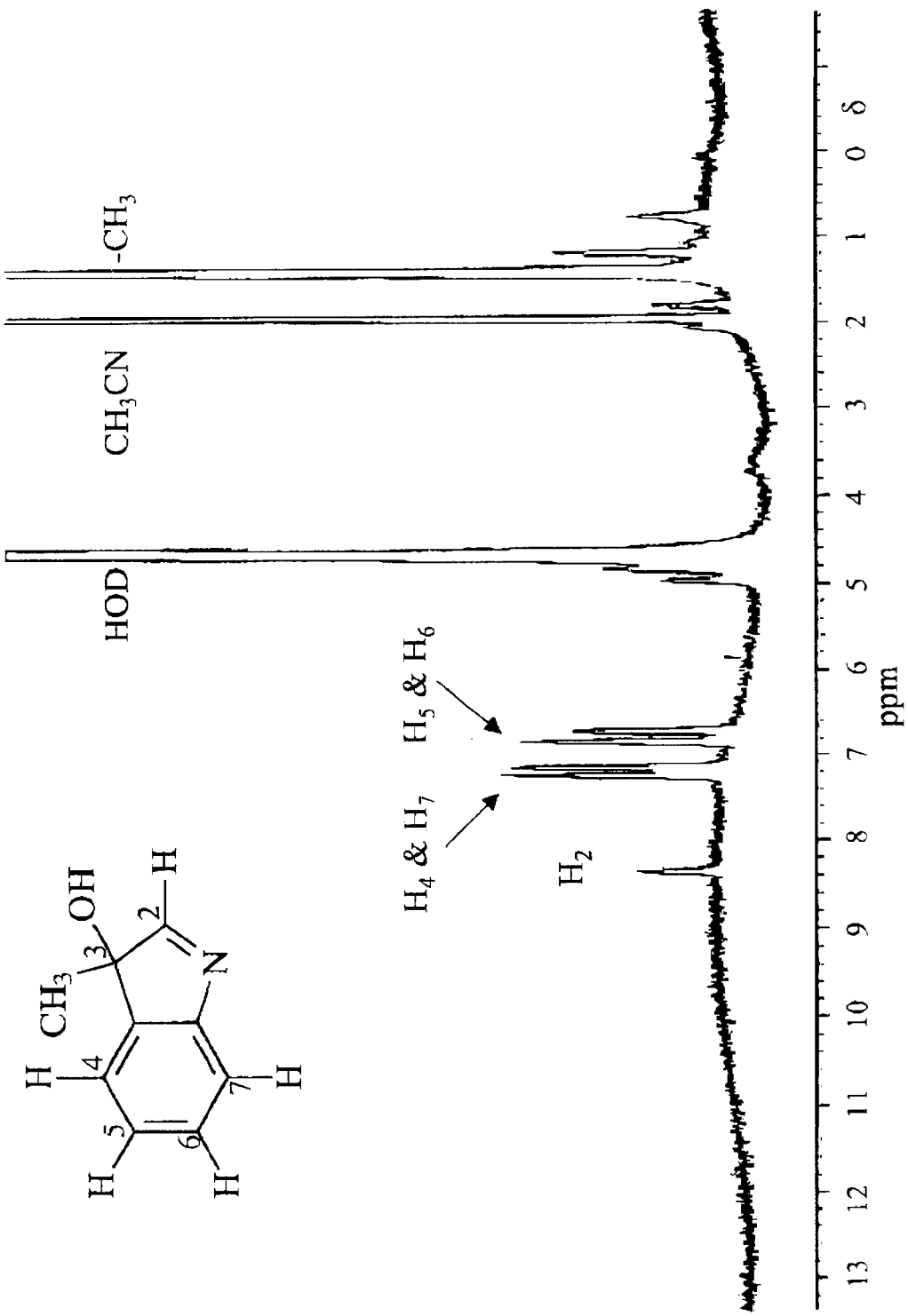
FIG. 4 is an $^1$H-NMR spectrum of metabolite UV-1.

Metabolite UV-1 structural data. The mass spectrometry of isolated UV-1 produced a molecular ion at m/z 148 $[M+H]^+$ with major fragments at m/z 133 $[M—CH_3]^+$, 104 $[M—H_3C—C—OH]^+$, and 77 (protonated phenyl ring) (FIG. 3). The $^1$H-NMR spectrum of metabolite UV-1 is shown in FIG. 4. Assignments of the proton signals are provided, listed as chemical shift (multiplicity, integration and assignment): 1.4 (s, 3H, —CH$_3$); 6.8 (d, 2H, H-5 and H-6); 7.2 (d, 2H, H-4 and H-7); 8.4 (s, 1H, H-2). The singlet at 8.4 has been assigned to the proton at C-2 of 3-hydroxy-3-methylindolenine. This proton is attached to the sp$^2$ hybridized C-2 which is also a deshielded by the adjacent nitrogen. Therefore, this proton is highly deshielded and appears downfield from all other protons in the proposed structure. At 2.0 is a singlet corresponding to the methyl protons of contaminating acetonitrile. Due to the way in which the sample was purified, it was extremely difficult to remove all of the acetonitrile present in the HPLC organic phase.

Figure 5:
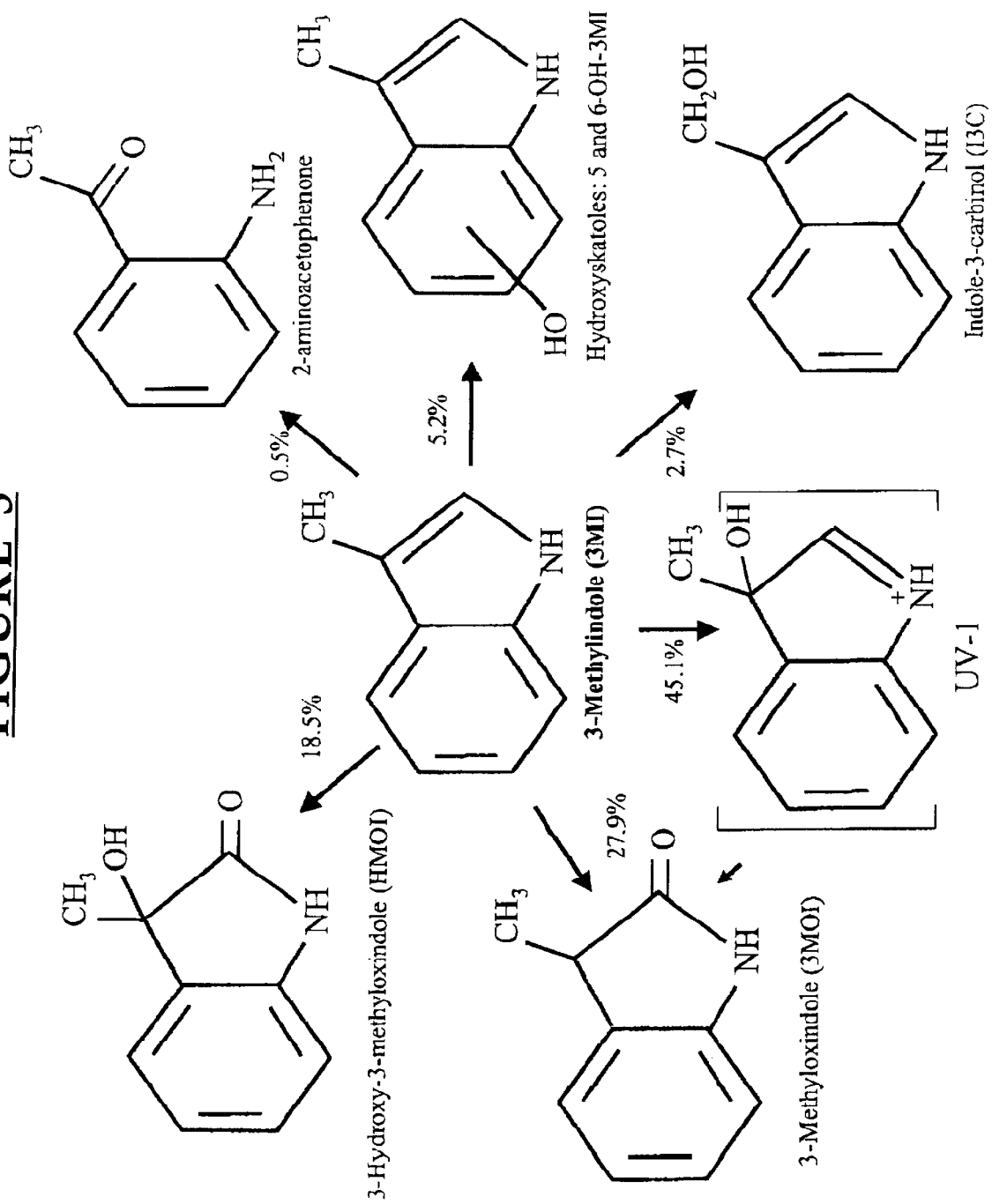
FIG. 5 shows chemical structures and percentages of 3MI metabolites produced by pig liver microsomes.

In summary, seven metabolites of 3MI were found to be produced by pig liver microsomes: 3MOI, HMOI, 6-OH-3-methylindole (6-OH-3MI), I3C, 2-aminoacetophenone, 5-OH-3-methylindole (5-OH-3MI), and the metabolite that was named UV-1. When UV-1 was quantitated assuming a molar absorptivity 2.95 times greater than that of 3MOI, the total amount of nanomoles produced accounted for an average of 96.0% (range of 86.5–105.0%) of the 3MI molecules metabolized during the microsomal incubations. The rates of production of the seven metabolites identified in pig liver microsomal incubations are shown in Table 1. UV-1 metabolite was produced at the highest rate (750.7 pmol/mg protein/min), while 5-OH-3MI was produced at the lowest rate (5.1 pmol/mg protein/min). Large inter-individual differences were noted for the production rates of the same metabolite. For instance, UV-1 metabolite was produced at a rate of 1556.3 pmol/mg protein/min by the microsomes of one pig, while other microsomes produced this compound at a rate of 180.5 pmol/mg/protein/min (Table 1). The metabolite that was produced in larger amounts was UV-1 which, on average, accounted for 45.1% of all metabolites produced. The combined oxindoles accounted for 46.4% of the total metabolites: an average of 27.9% of the metabolites produced corresponded to 3MOI whereas 18.5% corresponded to HMOI. The other metabolites were produced in much lesser amounts. 6-OH-3MI accounted for 4.9% of the metabolites, I3C accounted for 2.7% and 2-aminoacetophenone and 5-OH-3MI accounted for only 0.5% and 0.3% of the metabolites, respectively. The chemical structures and percentages of production of these metabolites are shown in FIG. 5.

Discussion

Only three Phase I metabolites of 3MI had been identified previously in pigs: HMOI, and the hydroxyskatoles, 5-OH-3MI and 6-OH-3MI. HMOI had been found in pig plasma and urine (Baek et al., 1997), and pig liver microsomal incubations (Babol et al., 1998a); 6-OH-3MI had been detected both in pig serum (Baek et al., 1997) and pig liver microsomal incubations (Babol et al., 1998a), while 5-OH-3MI had only been reported to be present in pig serum (Baek et al., 1997). In the present study, all three metabolites were detected in the microsomal incubations and the production of four new metabolites is reported.

One of the pathways of 3MI biotransformation identified in species such as goats, mice and rats is the formation of oxindole derivatives: 3MOI and HMOI (Frydman et al., 1972; Smith et al., 1993). On average, 46.4% of the metabolites produced by pig liver microsomes in the present study corresponded to these two oxindole derivatives; this finding indicates that the oxidole pathway is quantitatively very important in the pig. 3MOI had been identified in rat liver microsomal incubations (Frydman et al., 1972), goat lung and liver microsomal incubations (Huijzer et al., 1987), and in the urine of goats (Hammond et al., 1979). One of the metabolites observed in pig microsomal incubations by Babol et al. (1998a) was named "UV-3" and the results of the present study indicate this metabolite corresponds to 3MOI. The other oxindole derivative of 3MI, HMOI, had already been isolated from the urine of pigs dosed with 3MI (Baek et al., 1997) and was also reported to be produced by pig liver microsomes (Babol et al., 1998a); HMOI is also a major urinary metabolite produced by mice dosed with radiolabeled 3MI (Skiles et al., 1989), additionally it has been found in the urine of humans (Albrecht et al., 1989), and goats (Smith et al., 1993). Interestingly, in the present study, pig liver microsomes produced large amounts of both oxidole derivatives 3MOI and HMOI. In other species studied, one of these metabolites predominates. In goats, production of 3MOI predominates (Hammond et al., 1979), whereas in mice it is HMOI that predominates (Smith et al., 1993).

The 3 methyl group of 3MI may be oxidized to the alcohol, aldehyde and carboxylic acid functions (Hammond et al., 1979). In the present study, only the alcohol function of the 3 methyl group (indole-3-carbinol) was found to be produced by pig liver microsomes. This metabolite exhibits strong fluorescence and also absorbs in the UV and even though it had been previously reported to be produced by pig microsomes (named F-1 by Babol et al., 1998a), its structure was unknown. It is important to note that further metabolism of the alcohol function of indole-3-carbinol could possibly be catalyzed by alcohol dehydrogenase; if this is true, then the product of this reaction, indole-3-carboxaldehyde, would not be produced in microsomal incubations.

Hydroxylation of the aromatic ring of 3MI can occur at any of the carbons 4, 5, 6 or 7; however, the experimental evidence indicates that hydroxylation at positions 5 and 6 predominate. In 1962, Jepson and co-workers showed that rabbit liver microsomes hydroxylate tryptamine, indole acetic acid and related indoles to their corresponding 6-hydroxy derivatives. The microsomal system required NADPH and oxygen and did not form 5- or 7- hydroxyindoles (Jepson et al., 1962). Mahon and Mattok (1967) analyzed the urine of ten normal human subjects and found that all samples contained 6-hydroxyskatole and nine had the 5-isomer, although its excretion rate was approximately 50% of the 6-isomer; 7-hydroxyskatole was detected in three of the samples but its excretion rate was only 5% of the 6-isomer. None of the subjects excreted 4-hydroxyskatole (Mahon and Mattok, 1967). Baek et al. (1995) found conjugates of both 5-OH-3MI and 6-OH-3MI in pig serum. In the present study, the average rate of production of 6-OH-3MI was approximately eleven times greater than the production of the 5 isomer, indicating that hydroxylation at position C6 predominates.

Frydman et al. (1972) found two pyrrole ring opened metabolites produced after incubation of 3-MI with rat liver microsomes. The two compounds were identified as 2-formamidoacetophenone and 2-aminoacetophenone; a total of 33% of the metabolites formed corresponded to 2-formamidoacetophenone, 12% to 2-aminoacetophenone, and 5% to 3-MOI. In the present study, 2-aminoacetophenone was found to be produced by all liver samples analyzed at an average percentage of 0.5%, which is much lower than the percentage reported for rats by Frydman et al. (1972). No previous reports of 2-aminoacetophenone production from 3MI metabolism by pigs were found in the literature.

The $^1$H-NMR, LC-MS and UV-spectral characteristics of metabolite UV-1 indicate that this compound corresponds to 3-hydroxy-3-methylindolenine. UV-1 was found to be an unstable compound, intermediate between 3MI and 3MOI. The fact that UV-1 was converted into 3MOI suggested that this compound could be a precursor of 3MOI, possibly 2,3-epoxy-3-methylindolenine, the structure of which was postulated by Smith et al. (1993) or, most likely, its ring-opened product, 3-hydroxy-3-methylindolenine (Skordos et al., 1998a, 1998b). The molecular weight of the compound (147) and its fragmentation pattern were compatible with the epoxyde or the imine (FIG. 3), but the UV spectrum, with a $\lambda_{max}$ at 238 nm (FIG. 2) was more consistent with the imine structure. The molecular weight of 147 could also correspond to an aromatic phenolic metabolite of 3MI; however, when the UV spectrum of isolated UV-1 was taken under different pHs, it did not show the typical bathochromic shift observed in phenolic indoles. Furthermore, the fact that the UV spectrum of metabolite UV-1 was very similar to that of 3MOI and HMOI (FIG. 2) indicated that metabolite UV-1 could be structurally related to any of the two oxindoles; these metabolites, in which the pyrrol ring is oxidized at the 2-carbon position, show very different spectra than 3MI, or other metabolites such as I3C, 2-aminoacetophenone or the hydroxyskatoles. Finally, the $^1$H-NMR spectrum of UV-1 (FIG. 4) was consistent with the assignment of this metabolite to 3-hydroxy-3-methylindolenine.

The results of the present study indicate that seven major metabolites of 3MI are produced by pig liver microsomes in vitro. In quantitative terms, the main pathway of Phase I biotransformation of 3MI by pig liver microsomes appears to be the formation of oxindole derivatives and the formation of 3-hydroxy-3-methylindolenine. Differences in the metabolic fate of 3MI among species could explain the difference in species susceptibility to 3MI-induced lung toxicity. The extensive metabolism of 3MI to oxindole derivatives may explain the lack of pneumotoxicity showed by pigs and reported by Carlson and Yost (1989). The electrophilic metabolite 3-methylene-indolenine, which is the putative reactive metabolite of 3MI produced by cytochrome P-450 enzymes, is a precursor of I3C in lung microsomal incubations and susceptible species form I3C in appreciable amounts (Skiles and Yost, 1996). In the present in vitro study, less than 3% of the metabolites produced by pig liver microsomes corresponded to I3C, which may also explain the lack of susceptibility of pigs to suffer from 3MI-induced lung lesions. Large inter-individual differences in the rate of production of metabolites were observed. These differences in Phase I metabolism could be due to individual differences in cytochrome P450 enzymes and this issue should be further investigated. It was previously reported that CYP2E1 plays a role in the metabolism of 3MI in the pig (Squires and Lundstrom, 1997; Babol et al., 1998a), but the role of other isoenzymes remains to be determined. Babol et al. (1998b) reported sulfation and glucuronidation of some 3MI metabolites produced by pig liver microsomes. However, more studies are needed in order to determine the complete Phase II metabolism of the different metabolites of 3MI identified in the present study.

Example 2

Aldehyde Oxidase

Materials And Methods

Chemicals. Menadione, quinacrine and allopurinol were purchased from Sigma-Aldrich Canada (Oakville, ON, Canada). Authentic HMOI was graciously provided by Dr. G. S. Yost, Department of Pharmacology and Toxicology, University of Utah. HMI was produced using porcine liver microsomes and it was isolated and purified using preparative HPLC as described before (Diaz et al., 1999). Isolated HMI was freeze-dried and kept in a dessicator at −20° C. until used.

Preparation of porcine liver cytosol. Liver samples were taken from 30 intact male pigs obtained by back-crossing F3 European Wild Pig×Swedish Yorkshire boars with Swedish Yorkshire sows (Squires and Lundström, 1997). Liver samples were frozen in liquid nitrogen and stored at −80° C. For the preparation of the cytosolic fraction, partially thawed liver samples were finely minced and homogenized with 4 volumes of 0.05 M Tris-HCl buffer pH 7.4 (containing 0.15 M KCl, 1 mM EDTA, and 0.25 M sucrose) using a Ultra-Turax homogenizer (Janke and Kunkel, GDR). The homogenate was centrifuged at 10,000×g for 20 minutes and the resulting supernatant was centrifuged again at 100,000×g for 60 minutes in order to obtain the cytosolic fraction and the microsomal pellet. Cytosolic fractions were stored at −80° C. before analysis. Protein concentrations were determined by the method of Smith et al. (1985) using bicinchoninic acid protein assay reagents purchased from Pierce Chemical Co. (Rockford, Ill., USA) and bovine serum albumin as standard.

Enzyme assays. In order to investigate the role of AO in the conversion of HMI to HMOI, incubations containing HMI, porcine liver cytosol and different concentrations of the selected AO inhibitors menadione and quinacrine were conducted. Each incubation was run in duplicate, and were performed for three randomly selected cytosol porcine samples. HIMOI formation was detected and quantitated by HPLC as described under "Chromatographic analysis". AO activity was measured as the formation of HMOI per minute per mg of cytosolic protein. Assay mixtures contained 0.05M sodium phosphate buffer (pH 7.4) with 5 mM $MgCl_2$ and 1 mM EDTA, 1 mg cytosolic protein and 1 ug HMI in a final assay volume of 250 μl. For the inhibition experiments, different final concentrations of menadione (0, 2, 5, 10, 25, 50 and 100 μM) or quinacrine (0, 0.05, 0.1, 0.25, 0.5 and 1.0 mM) were tested in the assay mixture. Menadione was dissolved in ethanol (final assay concentration 4%, v/v), which had no effect on activity in controls without inhibitor; quinacrine was dissolved in buffer. Incubations were carried out for 10 min at 37° C. in a shaking water bath; the reaction was stopped with 250 μl ice-cold acetonitrile. After the addition of acetonitrile, the mixture was vortexed and centrifuged at 7,500 rpm for 15 min. A 400 μl aliquot of the clear supernatant was diluted with 400 μl water and 100 μl of the mixture were analyzed immediately by high-performance liquid chromatography (HPLC). Dilution with water was necessary in order to avoid leading of the chromatographic peaks. HMOI production was quantitated by using an external standard. Controls included incubations using boiled cytosol and incubations carried out without the addition of cytosol. Incubations run under the same conditions described above were conducted using 0.1, 0.5 and 1.0 mM allopurinol in order to investigate the role of XO on the enzymatic conversion of HMI into HMOI.

Chromatographic analysis. HPLC was conducted using a Spectra-Physics system (Spectra-Physics, San Jose, Calif., USA) consisting of a SP8800 gradient pump, a SP8880 autosampler with a 100 μl injection loop, and a SP Spectra 100 UV detector. The HPLC method is a modification of a previously reported binary gradient system method (Baek et al., 1997). HMOI and HMI were separated using a reverse-phase Prodigy ODS, 5 μm, 250×4.6 mm column (Phenomenex, Torrance, Calif., USA). The mobile phase consisted of two solvents, A (0.01M potassium dihydrogen phosphate buffer pH 3.9) and B (acetonitrile), with the following gradients: 0 min—90% A, 6 min—80% A; 12 min—70% A; 18 min—30% A; 25 min 10% A; 26 min 90% A; 35 min—90% A. All gradients were linear and the flow rate was set at 1.2 ml/min. Absorbance was monitored at 250 nm. HPLC analysis was conducted immediately after the incubations.

Measurement of 3MI fat content. For the quantitation of the 3MI fat content, a sample of backfat was taken from each pig and its 3MI content measured with a colorimetric assay (Mortensen and Sorensen, 1984). All analysis were done in duplicate.

Statistical analysis. Pearson correlation coefficients, linear regression analysis and one-way ANOVA were computed using the Statistical Analysis System (SAS, 1995).

Results

Figure 6:
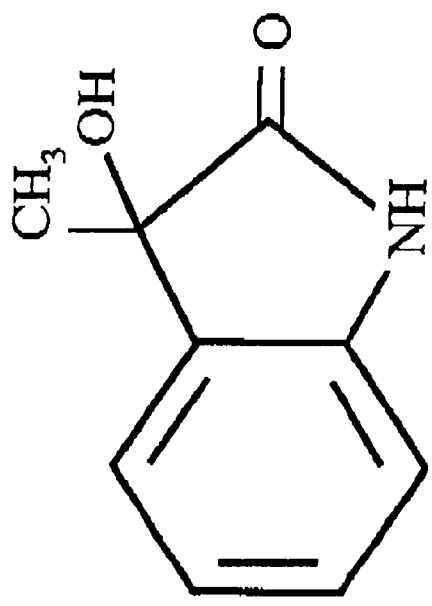
FIG. 6 shows the oxidative conversion of 3-hydroxy-3-methylindolenine into 3-hydroxy-3-methyloxindole catalyzed by aldehyde oxidase.
Figure 6:
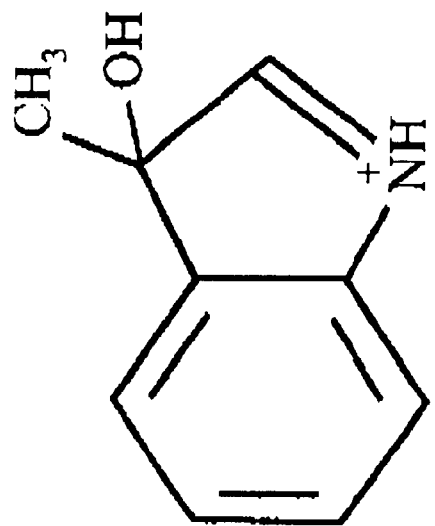
Figure 7:
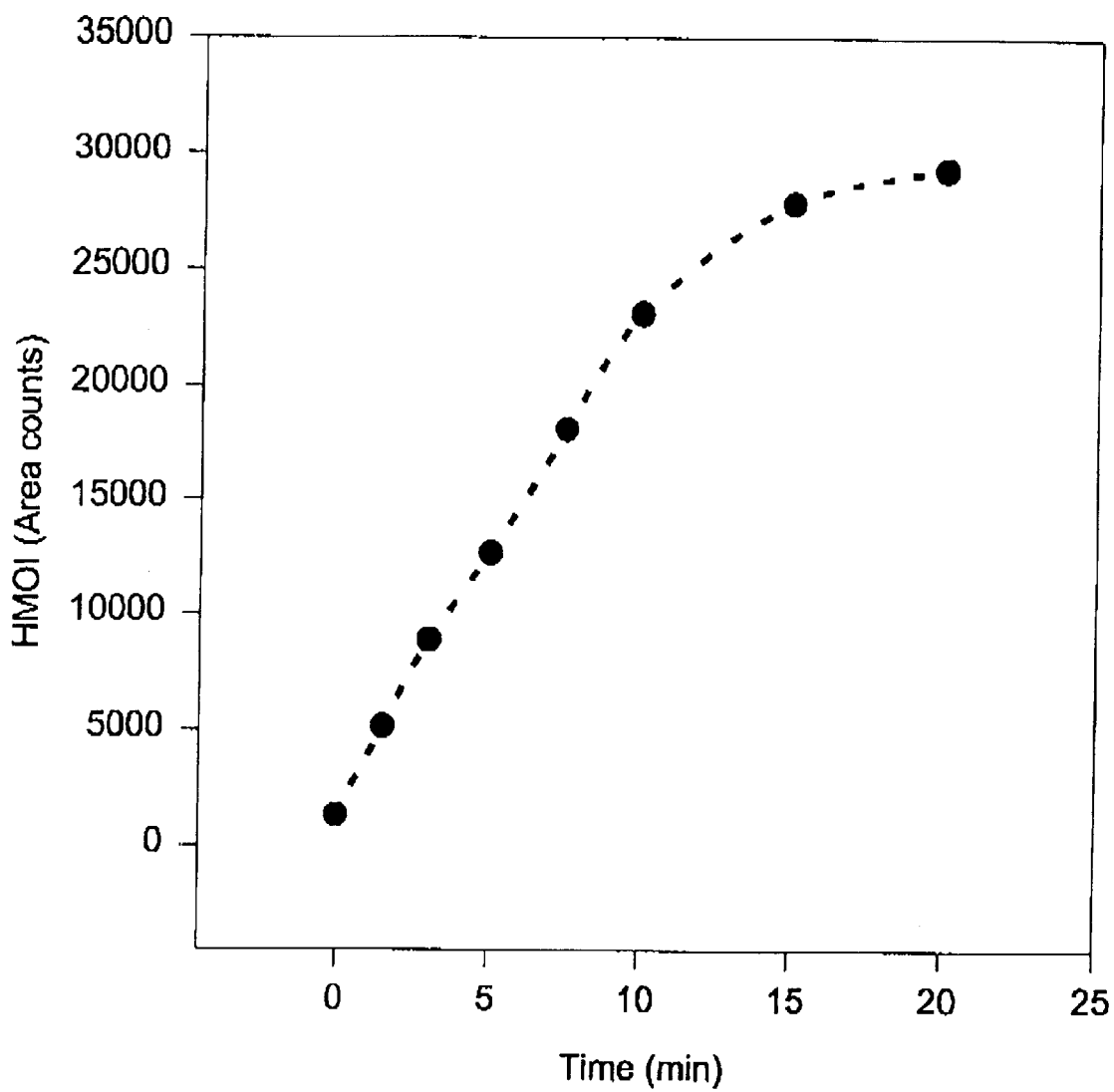
FIG. 7 shows the formation of 3-hydroxy-3-methyloxindole (HMOI) from 3-hydroxy-3-methylindolenine, catalyzed by porcine cytosol. Each data point represents the mean of duplicate assays performed for three pigs.
Figure 8:
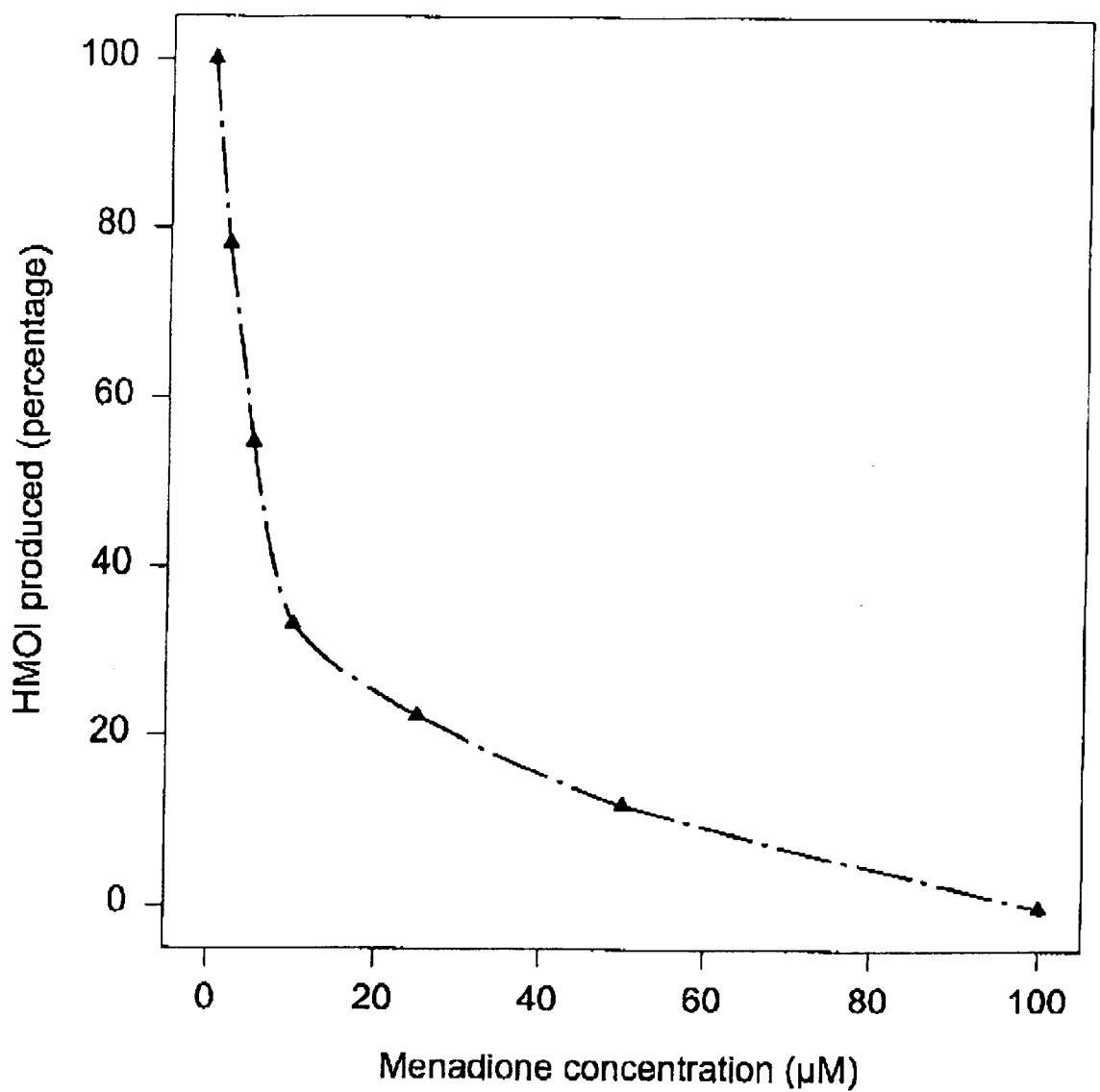
FIG. 8 shows the menadione-induced inhibition of the formation of 3-hydroxy-3-methyloxindole (HMOI) from 3-hydroxy-3-methylindolenine. Each data point represents the mean of duplicate assays performed for three pigs.
Figure 9:
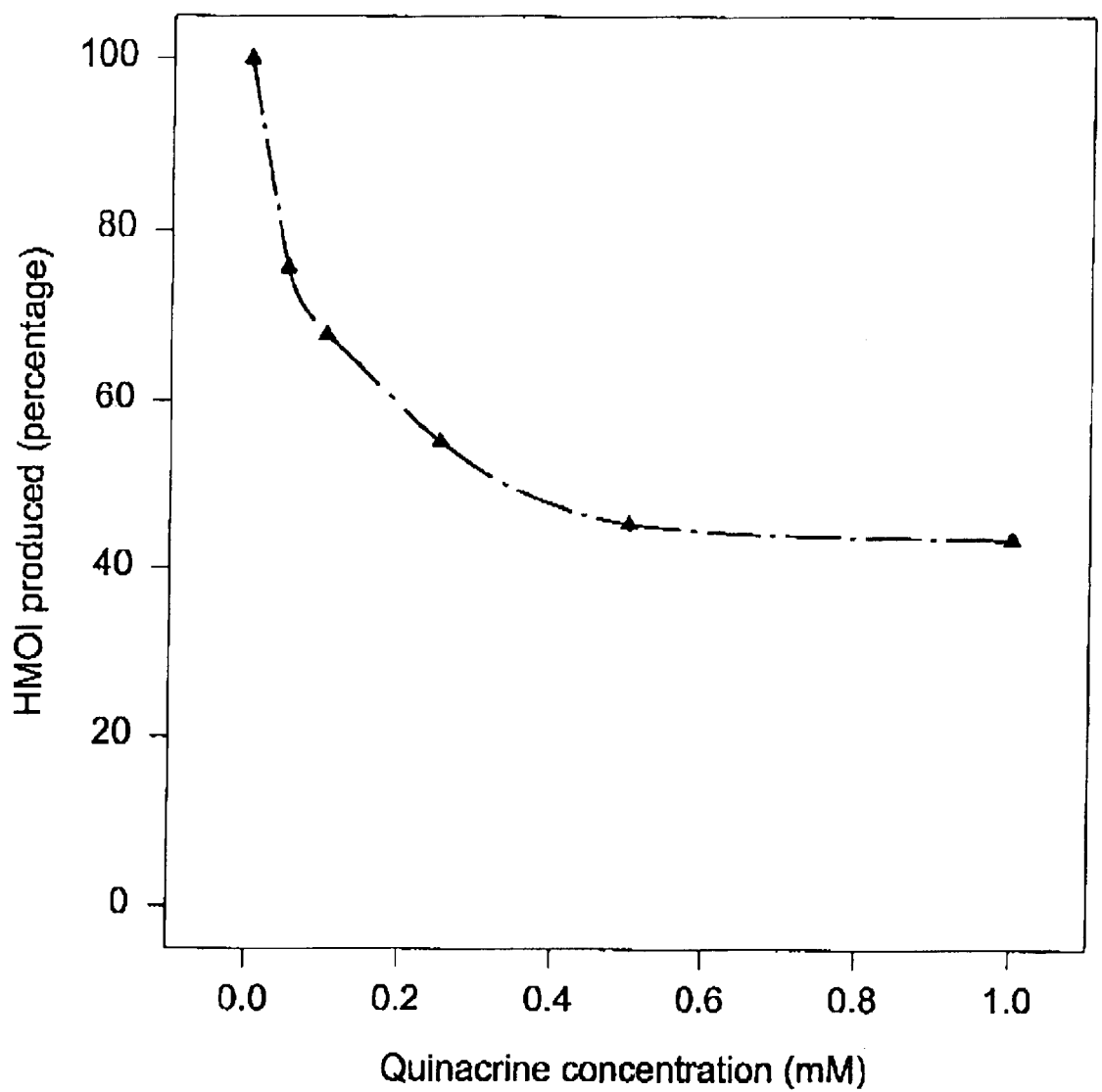
FIG. 9 shows the quinacrine-induced inhibition of the formation of 3-hydroxy-3-methyloxindole (HMOI) from 3-hydroxy-3-methylindolenine. Each data point represents the mean of duplicate assays performed for three pigs.

Porcine cytosol catalyzed the conversion of HMI to HMOI (FIG. 6) in a time-dependent manner (FIG. 7). Under these assay conditions, the formation of HMOI was found to be linear ($r^2$=0.995) up to 10 min (FIG. 7). No HMOI was formed when cytosol was boiled before the incubation or when no cytosol was added to the assay mixture. The addition of the aldehyde-oxidase inhibitors menadione or quinacrine to the incubation mixtures containing HMI and cytosolic protein decreased the formation of HMOI in a dose-dependent manner. When no inhibitor was added, the total amount of HMOI produced was considered as 100%. At a concentration of 10 μM menadione, only 33.3% of the HMOI formed in the absence of menadione was detected whereas at a concentration of 100 μM menadione, no HMOI was produced (FIG. 8). At a concentration of 50 μM quinacrine, 75.5% of the control HMOI production was observed and at 1 mM 43.4% of the control HMOI was found (FIG. 9). Menadione was a more potent inhibitor of the reaction since even a concentration of quinacrine 10 times higher than that of menadione (1 mM vs 100 μM) was not enough to completely abolish the conversion of HMI to HMOI. The addition of up to 1.0 mM allopurinol to the assay mixture did not affect the conversion of HMI to HMOI (data not shown).

Figure 10:
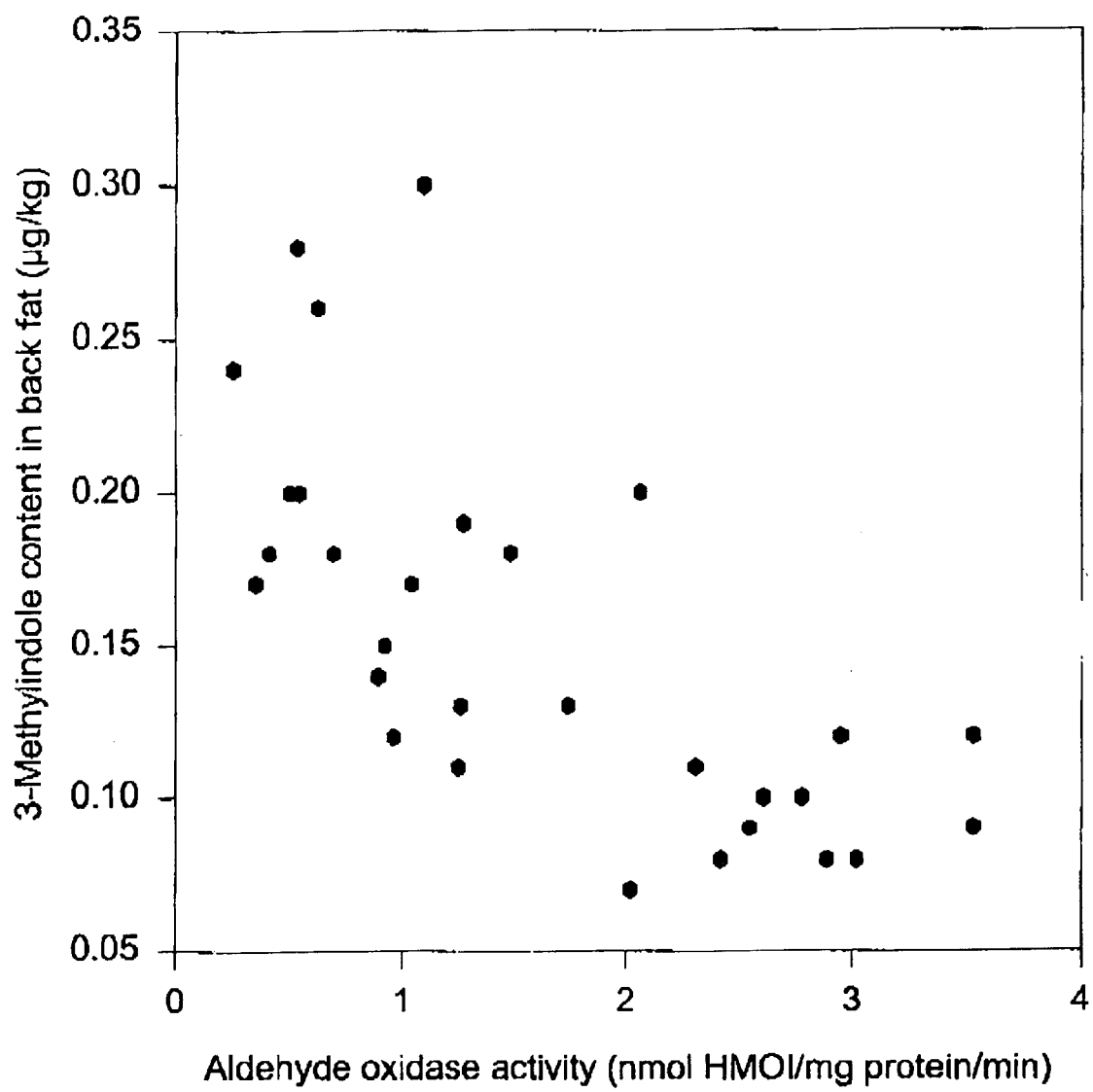
FIG. 10 shows the plot of back fat 3-methylindole content versus hepatic aldehyde oxidase activity in pigs (n=30). Aldehyde oxidase activity measured as nmol of 3-hydroxy-3-methyloxindole (HMOI) formed per mg of cytosolic protein per min.

The AO activity, estimated as nmol of HMOI produced per minute per mg cytosolic protein, versus the 3MI fat content of the 30 pigs used in this study are shown in FIG. 10. The Pearson correlation coefficient between these two variables was found to be −0.70 (P<0.001), whereas the determination coefficient was $r^2$=0.49. The linear regression model to explain the 3MI fat content as a function of AO activity was found to be: 3MI in fat=0.22—AO activity 0.042763. This model was found to be highly significant (P<0.001).

The 3MI fat content in all samples ranged from 0.07 to 0.3 mg/kg and had mean value of 0.15 mg/kg, whereas the AO activity ranged from 0.25 to 3.53 nmol HMOI/mg protein/ min and had a mean value of 1.27 nmol HMOI/mg protein/ min. The results were grouped in three categories according to the 3MI fat content of each pig as follows: large 3MI accumulators (0.2 mg/kg 3MI or more), moderate 3MI accumulators (0.11 to 0.19 mg/kg 3MI) and low accumulators (0.1 mg/kg 3MI or less). Lundström and Bonneau (1996) have suggested that levels of 3MI of 0.2–0.25 mg/kg or greater cause unacceptable taint by sensory analysis. The mean values for 3MI fat content and AO activity for these three categories of pigs are shown in Table 2.

Discussion

Menadione is a well documented inhibitor of AO (Johns, 1967; Krenitzky et al., 1974; Rodrigues, 1994) and biochemical reactions sensitive to inhibition by menadione are attributed to AO (Beedham et al., 1995; Rashidi et al., 1997). Rodrigues (1994) found that at a concentration of 10 μM, menadione completely abolished the oxidation of $N^1$-methylnicotinamide, the model substrate for AO. In the present experiment, a concentration of 10 μM menadione decreased the formation of HMOI by 56.7%, and at 100 μM menadione, no HMOI was formed, indicating a complete inhibition of the enzymatic activity. The inverse dose-response relationship observed between HMOI production and menadione concentration strongly suggests that AO is the enzyme responsible for the biotransformation of HMI into HMOI in porcine cytosol. Quinacrine has been reported as being a competitive inhibitor ($K_i$=1.5×10$^{-6}$ M) of aldehyde oxidase against all substrates (Rajagopalan and Handler, 1964). In the present trial, quinacrine was less potent than menadione in inhibiting the conversion of HMI into HMOI but it also inhibited the reaction to a large extent. The inhibition of HMOI formation caused by quinacrine also suggests that the production of HMOI from HMI is catalyzed by AO. On the other hand, the lack of inhibition observed when allopurinol was added to the reaction mixture indicates that XO is not involved in the oxidative metabolism of HMI into HMOI.

N-heterocyclic cations constitute a major group of substrates for AO (Beedham, 1985). Quaternization of a ring nitrogen atom activates the heterocycle to nucleophilic substitution and enhances the reactivity of the compound toward enzyme-catalyzed attack (Beedham, 1985). HMI is a recently identified N-heterocyclic quaternized metabolite produced by porcine microsomal enzymes (Diaz et al., 1999) and therefore it constitutes a suitable substrate for AO-catalyzed oxidation. The results of the present study strongly suggest that AO activity present in the cytosol of pigs is responsible for the oxidation of HMI to form a more polar and stable metabolite, HMOI.

When hepatic AO activity (measured as the formation of HMOI) was plotted against the 3MI fat content, a clear inverse relationship was observed (FIG. 9). This finding suggests that hepatic AO activity is related to 3MI clearance. The relatively high determination coefficient ($r^2$=0.49) indicates that almost 50% of the variation in 3MI fat content is explained by the hepatic enzymatic activity of AO. The results shown on Table 2 also indicate that AO activity may be very significant in the adequate clearance of 3MI in the pig. High 3MI fat levels were associated with low enzymatic activity (mean values of 0.24 mg/kg 3MI and 0.80 nmol HMOI/mg protein/min, respectively), whereas low 3MI levels were associated with high enzymatic activity (mean values of 0.09 mg/kg 3MI and 2.73 nmol HMOI/mg protein/ min, respectively). Pigs classified as high 3MI accumulators had a hepatic mean AO activity 3.4 times lower than those pigs classified as low accumulators; this difference was found to be significant (P<0.05).

The results of the present study suggest that AO plays an important role in the metabolism of 3MI in the pig and that its catalytic activity is related to an adequate 3MI clearance. The enzymatic activity of AO in the pig might be used as a potential marker in order to identify pigs containing low levels of 3MI in the fat, which will eventually help to control "boar taint".

Menadione is customarily used as a source of vitamin K in swine diets (National Research Council, 1987). Recommended levels of inclusion are 2.5 mg/kg for grower diets and 2.0 mg/kg for finisher diets (Patience et al., 1995). Since menadione is a potent inhibitor of AO and the enzyme appears to be important in the metabolism of 3MI, care should be exercised so that excessive levels of menadione are not present in swine diets. It is possible that some of the sporadic episodes of "boar taint" could had been caused by high levels of menadione in the diet resulting in high levels of 3MI in the fat of pigs. Studies are needed in order to determine whether the levels of menadione commonly used in practical pig diets are capable of inhibiting AO activity. Additionally, it has been observed that high levels of dietary copper lead to molybdenum deficiency and thus to low AO activity because molybdenum is a cofactor for this enzyme (Beedham, 1985). It is important to avoid excess copper levels in pig diets in order to avoid a decrease in the activity of AO and the potential occurrence of "boar taint" episodes.

Example 3

The Role of CYP2A6 in 3-Methylindole Metabolism by Porcine Liver Microsomes

The role of different cytochrome P450 enzymes on the metabolism of 3-methylindole (3MI) was investigated using selective chemical inhibitors. Eight chemical inhibitors of P450 enzymes were screened for their inhibitory specificity towards 3MI metabolism in porcine microsomes: alpha-naphthoflavone (CYP1A2), 8-methoxypsoralen (CYP2A6), menthofuran (CYP2A6), sulphaphenazole (CYP2C9), quinidine (CYP2D6), 4-methylpyrazole (CYP2E1), diethyldithiocarbamate (CYP2E1, CYP2A6), and troleandomycin (CYP3A4). The production of the different 3MI metabolites was only affected by the presence of inhibitors of CYP2E1 and CYP2A6 in the microsomal incubations. In a second experiment, a set of porcine microsomes (n=30) was screened for CYP2A6 content by Western blot analysis and also for their 7-hydroxylation activity (CYP2A6 activity). Protein content and enzymatic activity were found to be correlated with 3MI fat content. The results of the present study indicate that measurement of CYP2A6 levels and/or activity is a useful marker for 3MI-induced boar taint.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Rate of production of 3MI metabolites by pig liver microsomes (pmol/mg microsomal protein/min) (n = 30)

| Production (pmol/mg prot./ Metabolite | Rate of Minimum (pmol/mg min) ± SD | Maximum (pmol/mg prot./min) | prot./min) |
|---|---|---|---|
| UV-1 | 750.7 ± 414.5 | 180.5 | 1556.3 |
| 3-methyloxindole | 420.9 ± 118.1 | 234.4 | 700.8 |
| 3-hydroxy-3-methyloxindole | 272.4 ± 91.6 | 118.9 | 516.5 |
| 6-OH-3-methylindole | 58.4 ± 47.2 | n.d.* | 213.7 |
| Indole-3-carbinol | 37.1 ± 15.8 | 12.1 | 85.7 |
| 2-aminoacetophenone | 7.8 ± 2.4 | 3.4 | 12.7 |
| 5-OH-3-methylindole | 5.1 ± 5.8 | 0.7 | 27.3 |

*n.d. = not detected

TABLE 2

Hepatic aldehyde oxidase activity in pigs with different 3-methylindole fat content

| Category | 3-Methylindole fat content | n | Mean (SD) 3-Methylindole content (mg/kg) | Mean (SD) aldehyde oxidase activity (nmol HMOI/mg prot./min) |
|---|---|---|---|---|
| High accumulator | 0.2 mg/kg or more | 7 | 0.24 0.04$^a$ | 0.80 061$^b$ |
| Moderate accumulator | 0.11–0.19 mg/kg | 15 | 0.15 003$^b$ | 1.40 0.90$^b$ |
| Low accumulator | 0.1 mg/kg or less | 8 | 0.09 0.01$^c$ | 2.73 0.45$^a$ |

$^{a-c}$Within a column, means lacking a common superscript differ significantly (P < 0.05).

FULL CITATIONS FOR REFERENCES REFERRED TO IN THE SPECIFICATION

Aitio, A. (1978) A simple and sensitive assay of 7-ethoxycoumarin deethylation. Anal. Biochem. 85, 488–491.

Albrecht C F, Chorn D J and Wessels P (1989) Detection of 3-hydroxy-3-methyloxindole in human urine. Life Sci 45:1119–1126.

Babol J, Squires E J and Lundström K (1998a) Hepatic metabolism of skatole in pigs by cytochrome P4502E1. J Anim Sci 76:822–828.

Babol J, Squires E J and Lundström K (1998b) Relationship between oxidation and conjugation metabolism of skatole in pig liver and concentrations of skatole in fat. J Anim Sci 76:829–838.

Bæk C E, Hansen-Mller J, Friis C and Hansen S H (1995) Identification and quantification of selected metabolites of skatole—possibilities for metabolic profiling of pigs. Proc. EAAP Working Group Production and Utilisation of Meat from Entire Male Pigs, Milton Keynes, INRA and MLC.

Bæk E, Hansen-Mller J, Friis C, Cornett C and Hansen S H (1997) Identification of selected metabolites of skatole in plasma and urine from pigs. J Agric Food Chem 45:2332–2340.

Beedham, C. (1985) Molybdenum hydroxylases as drug-metabolizing enzymes. Drug Metab. Rev., 16, 119–156.

Beedham, C.; Peet, C. F.; Panoutsopoulos, G. I.; Carter, H.; Smith, J. A. (1995) Role of aldehyde oxidase in biogenic amine metabolism. Prog. Brain Res., 106, 345–353.

Bonneau, M. 1997. Proc. EAAP Working Group on the Production and Utilization of Meat from Entire Male Pigs, Stockholm.

Carlson J R and Yost G S (1989) 3-Methylindole-induced acute lung injury resulting from ruminal fermentation of tryptophan, in *Toxicants of Plant Origin. Volume III. Protein and Amino Acids* (Cheeke PR ed) pp 107–123, CRC Press, Boca Raton.

Claus, R., U. Weiler, and A. Herzog. 1994. Physiological aspects of androstenone and skatole formation in the boar—a review with experimental data. Meat Sci. 38:289–305.

Diaz, G. J.; Skordos, K.; Yost, G. S; Squires, E. J. (1999, in press) Identification of Phase I metabolites of 3-methylindole produced by pig liver microsomes. *Drug Metab. Dispos.*

Friis, C. 1993. Distribution, metabolic fate and elimination of skatole in the pig. In: M. Bonneau (Ed.) Measurement and prevention of boar taint in intact male pigs. p 113–115. INRA Edition, Paris.

Frydman R B, Tomaro M L and Frydman B (1972) Pyrrolooxygenases: isolation, properties, and products formed. *Biochim Biophys Acta* 284:63–79.

Hammond A C, Carlson J R and Willett J D (1979) The metabolism and disposition of 3-methylindole in goats. *Life Sci* 25:1301–1306.

Hansen L L, Larsen A E and Hansen-Møller J (1995) Influence of keeping pigs heavily fouled with faeces plus urine on skatole and indole concentration (boar taint) in subcutaneous fat. *Acta Agric Scand* 45:178–185.

Huijzer J C, Adams J D and Yost G S (1987) Decreased pneumotoxicity of deuterated 3-methylindole: bioactivation requires methyl C—H bond breakage. *Toxicol Appl Pharmacol* 90:60–68.

Jensen M T, Cox R P and Jensen B B (1995) Microbial production of skatole in the hind gut of pigs given different diets and its relation to skatole deposition in backfat. *Anim Sci* 61:293–304.

Jepson J B, Zaltzman P and Udenfriend S (1962) Microsomal hydroxylation of tryptamine, indole acetic acid and related compounds, to 6-hydroxy derivatives. *Biochim Biophys Acta* 62:91–102.

Johns, D. G. (1967) Human liver aldehyde oxidase: differential inhibition of oxidation of charged and uncharged substrates. *J. Clin. Invest.*, 46, 1492–1505.

Kende A S and Hodges J C (1982) Regioselective C-3 alkylations of oxindole dianion. *Synth Commun* 12:1–10.

Kjeldsen, N. 1993. Practical experience with production and slaughter of intact male pigs. In: M. Bonneau (Ed.) Measurement and prevention of boar taint in intact male pigs. p 137–144. INRA Edition, Paris.

Krenitsky, T. A.; Tuttle, J. V.; Cattau, E. L. Jr.; Wang, P. (1974) A comparison of the distribution and electron acceptor specificities of xanthine oxidase and aldehyde oxidase. Comp. *Biochem. Physiol.*, 49B, 687–703.

Lundström, K.; Bonneau, M. (1996) Off-flavour in meat with particular emphasis on boar taint. In *Meat Quality and Meat Packaging*; Taylor, S., Raimundo A., Severini, M.; Smulders, F. J. M., Eds., ECCEAMST, Utrecht.

Lundström, K., B. Malmfors, S. Stern, L. Rydhmer, L. Eliasson-Selling, A. B. Mortensen, and H. P. Mortensen. 1994. Skatole levels in pigs selected for high lean tissue growth rate on different protein levels. Livest. Prod. Sci. 38:125–132.

Mahon M E and Mattok G L (1967) The differential determination of conjugated hydroxyskatoles in human urine. *Can J Biochem* 45:1317–1322. Ruangyuttikarn W, Appleton M L and Yost G S (1991) Metabolism of 3-methylindole in human tissues. *Drug Metab Dispos* 19:977–984.

Mortensen, A. B.; Sørensen, S. E. (1984) Relationship between boar taint and skatole determination with a new analysis method. Proc. $30^{th}$ Eur. Mtg. Res. Workers, Bristol. Paper 8–11, p. 395.

National Research Council. (1987) *Vitamin Tolerance of Animals*. National Academy Press, Washington.

Patience, J. F.; Thacker, P. A.; de Lange C. F. M. (1995) *Swine Nutrition Guide*. $2^{nd}$ Ed. Prairie Swine Centre Inc., Saskatoon.

Rajagopalan, K. V.; Handler, P. (1964) Hepatic aldehyde oxidase. III. The substrate binding site. *J. Biol. Chem.*, 239, 2027–2035.

Rajagopalan, K. V.; Handler, P. (1966) P. Aldehyde oxidase. Methods Enzymol. 9, 364–368.

Rashidi, M. R.; Smith, J. A.; Clarke, S. E.; Beedham, C. (1997) In vitro oxidation of famciclovir and 6-deoxypenciclovir by aldehyde oxidase from human, guinea pig, rabbit, and rat liver. *Drug Metab. Dispos.*, 25, 805–813.

Rodrigues, A. D. (1994) Comparison of levels of aldehyde oxidase with cytochrome P450 activities in human liver in vitro. *Biochem. Pharmacol.*, 48,197–200.

SAS. (1995) SAS System for Windows (Release 6.11). SAS Institute Inc., Cary, N.C.

Sambrook et al. (1989) Molecular Cloning A Laboratory Manual, 2nd edition, Cold Spring Harbor Laboratory Press Skiles G L and Yost G S (1996) Mechanistic studies on the cytochrome P450-catalyzed dehydrogenation of 3-methylindole. *Chem Res Toxicol* 9:291–297.

Skiles G L, Adams J D and Yost G S (1989) Isolation and identification of 3-hydroxy-3-methyloxindole, the major murine metabolite of 3-methylindole. *Chem Res Toxicol* 2:254–259.

Skordos K W, Skiles G L, Laycock J D, Lanza D L and Yost G S (1998a) Evidence supporting the formation of 2,3-epoxy-3-methylindoline: a reactive intermediate of the pneumotoxin 3-methylindole. *Chem Res Toxicol* 11:741–749.

Skordos K W, Laycock J D and Yost G S (1998b) Thioether adducts of a new imine reactive intermediate of the pneumotoxin 3-methylindole. *Chem Res Toxicol* 11:1326–1231.

Smith P K, Krohn R I, Hermanson G T, Mallia A K, Gartner F H, Provenzano M D, Fujimoto E K, Goeke N M, Olson B J and Klenk D C (1985) Measurement of protein using bicinchoninic acid. *Anal Biochem* 150:76–85.

Smith D J, Skiles G L, Appleton M L, Carlson J R and Yost G S (1993) Identification of goat and mouse urinary metabolites of the pneumotoxin, 3 methylindole. *Xenobiotica* 23:1025–1044.

Squires E J and Lundström K (1997) Relationship between cytochrome P450IIE1 in liver and levels of skatole and its metabolites in intact male pigs. *J Anim Sci* 75:2506–2511.

We claim:

1. A method of assessing a pig's ability to metabolize 3-methyl indole comprising testing a sample from the pig for (a) one or more metabolites selected from the group consisting of 3-OH-3-methylindolenine (HMI); 3-methyloxindole (3MOI); indole-3-carbinol (I-3C); and 2 aminoacetophenone; (b) aldehyde oxidase activity; and/or (c) CYP2A6 activity, wherein (a) the presence of one or more metabolites; (b) high aldehyde oxidase activity and/or (c) high CYP2A6 activity indicates that metabolize 3-methylindole, and high aldehyde oxidase activity and/or high CYP2A6 activity is any activity that is greater than an activity that is correlated with a level of 3-methyl indole in the fat that is greater than about 0.2 mg/kg.

2. A method according to claim 1 wherein the sample is from liver, plasma or fat.

3. A method according to claim 1 for determining a pig's susceptibility to boar taint wherein the ability to metabolize 3-methylindole indicates that the pig is at a reduced risk for boar taint.

* * * * *